(12) United States Patent
Kumar et al.

(10) Patent No.: US 8,709,420 B2
(45) Date of Patent: Apr. 29, 2014

(54) PHARMACEUTICAL COMBINATION OF PAZOPANIB AND TOPOTECAN TO TREAT NEUROBLASTOMA, OSTEOSARCOMA, AND RHABDOMYOSARCOMA IN A HUMAN

(75) Inventors: Rakesh Kumar, Collegeville, PA (US); Sylvain Baruchel, Durham, NC (US)

(73) Assignee: GlaxoSmithKline Intellectual Property Limited, Brentford, Middlesex (GB)

( * ) Notice: Subject to any disclaimer, the term of this patent is extended or adjusted under 35 U.S.C. 154(b) by 0 days.

(21) Appl. No.: 13/990,515

(22) PCT Filed: Nov. 23, 2011

(86) PCT No.: PCT/US2011/061985
§ 371 (c)(1), (2), (4) Date: May 30, 2013

(87) PCT Pub. No.: WO2012/082337
PCT Pub. Date: Jun. 21, 2012

(65) Prior Publication Data
US 2013/0252991 A1 Sep. 26, 2013

Related U.S. Application Data

(60) Provisional application No. 61/424,254, filed on Dec. 17, 2010, provisional application No. 61/467,078, filed on Mar. 24, 2011.

(51) Int. Cl.
*A61K 45/06* (2006.01)

(52) U.S. Cl.
USPC .......................................................... 424/133.1

(58) Field of Classification Search
None
See application file for complete search history.

(56) References Cited

U.S. PATENT DOCUMENTS

| | | | |
|---|---|---|---|
| 5,004,758 A | 4/1991 | Boehm et al. | |
| 2006/0216288 A1 | 9/2006 | Chang | |
| 2009/0209496 A1* | 8/2009 | Chaplin et al. | 514/130 |
| 2010/0249127 A1 | 9/2010 | Namdev et al. | |
| 2010/0297075 A1* | 11/2010 | Chan et al. | 424/85.4 |

FOREIGN PATENT DOCUMENTS

| WO | WO 02/059110 | 8/2002 |
|---|---|---|
| WO | WO 2012/106302 | 8/2012 |

* cited by examiner

*Primary Examiner* — San-Ming Hui
*Assistant Examiner* — Jeanmarie Calvillo
(74) *Attorney, Agent, or Firm* — Robert H. Brink

(57) ABSTRACT

The present invention relates to methods of treating neuroblastoma, osteosarcoma, and rhabdomyosarcoma in a human and to pharmaceutical combinations useful in such treatment. In particular, the method relates to a neuroblastoma treatment method that includes administering 5-[[4-[(2,3-dimethyl-2H-indazol-6-yl)methylamino]-2-pyrimidinyl]amino]-2-methylbenzenesulfonamide, or a pharmaceutically acceptable salt thereof, and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt thereof, to a human in need thereof.

10 Claims, 34 Drawing Sheets

Figure 12
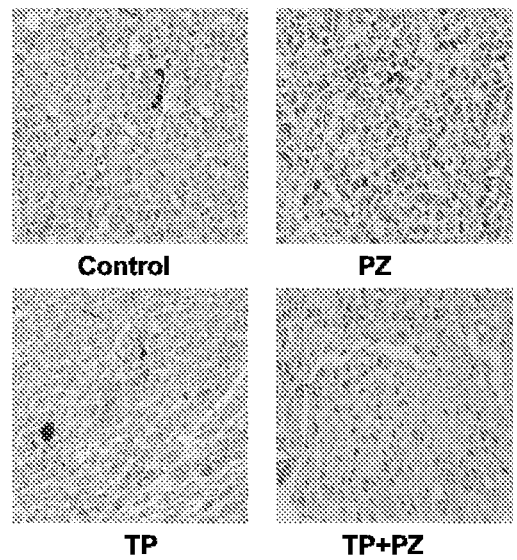
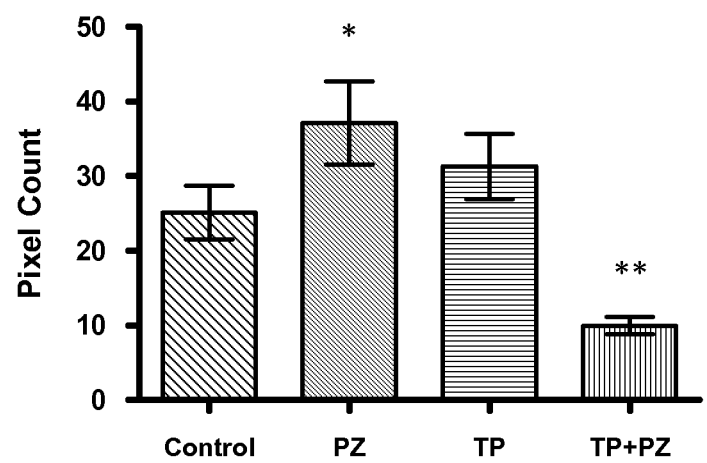

Figure 13
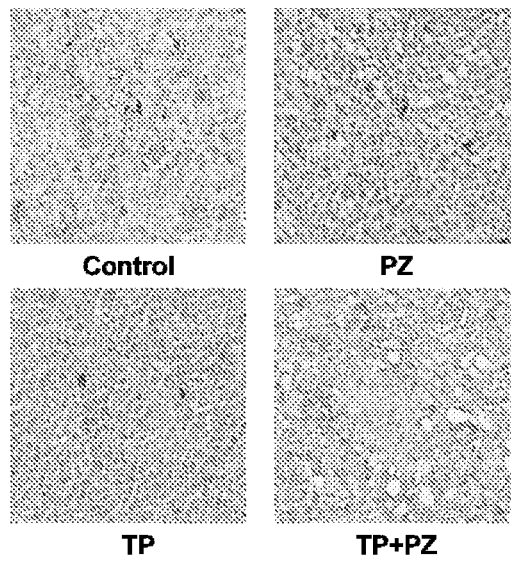
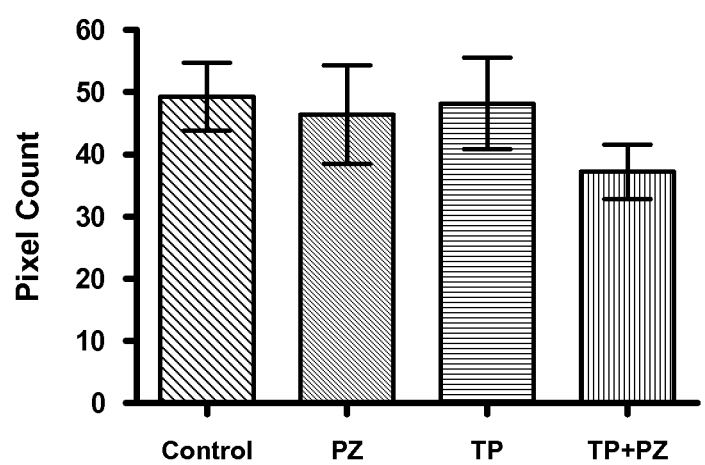

Figure 14
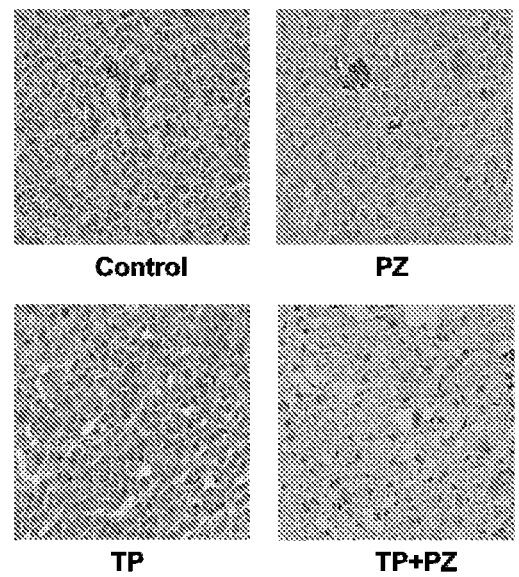
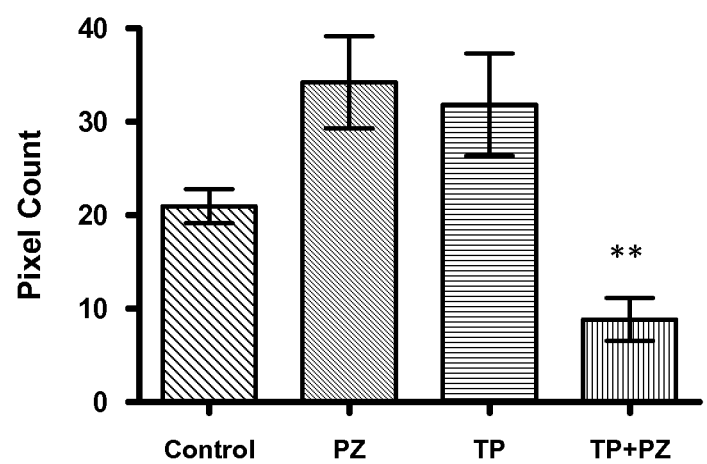

Figure 21
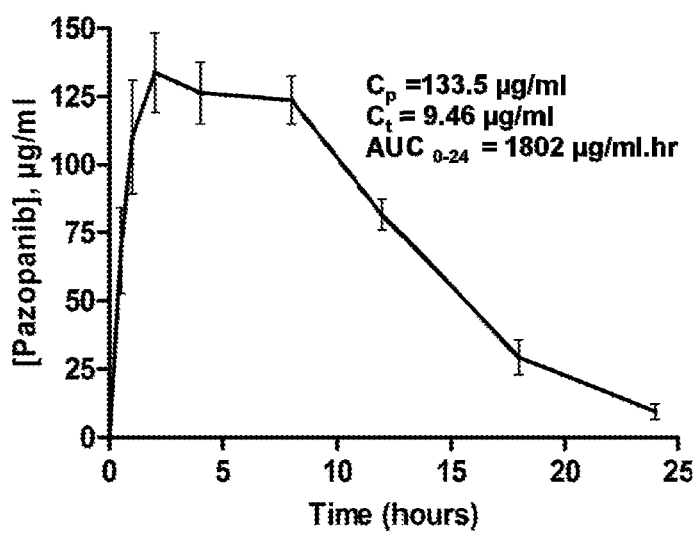
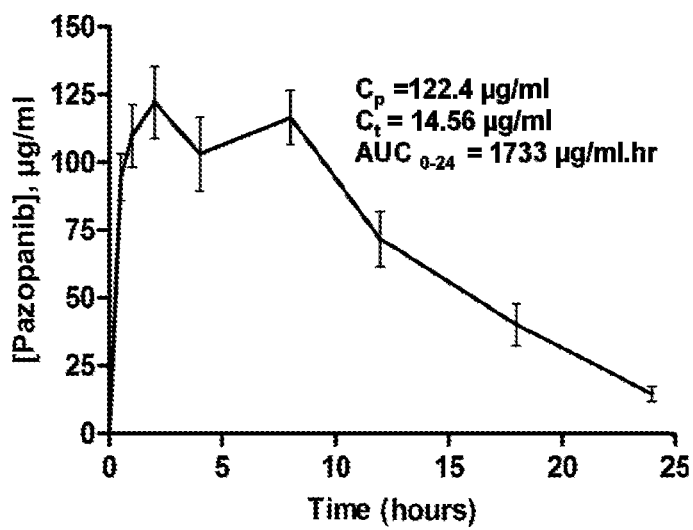

Figure 23A
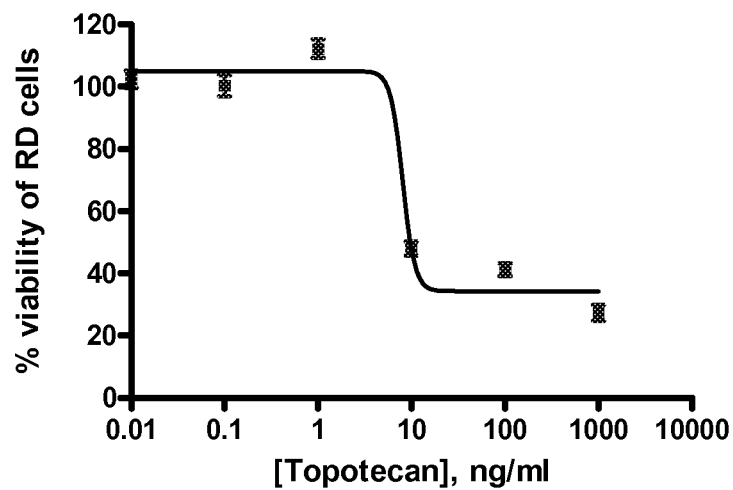
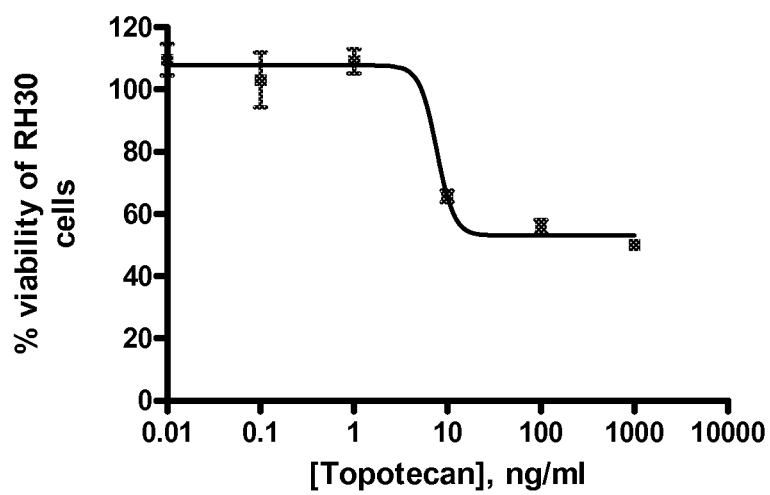

Tumor growth rate in RH30 rhabdomyosarcoma model

PHARMACEUTICAL COMBINATION OF PAZOPANIB AND TOPOTECAN TO TREAT NEUROBLASTOMA, OSTEOSARCOMA, AND RHABDOMYOSARCOMA IN A HUMAN

CROSS-REFERENCE TO RELATED APPLICATIONS

This application is filed pursuant to 35 USC 371 as a United States National Phase Application of International Patent Application Serial No. PCT/US2011/061985 filed on Nov. 23, 2011, which claims priority from 61/467,078 filed on Mar. 24, 2011 and 61/424,254 filed on Dec. 17, 2010 in the United States.

FIELD OF THE INVENTION

The present invention relates to a method of treating cancer in a mammal and to combinations useful in such treatment. In particular, the method relates to a novel combination comprising a VEGFR inhibitor and a topoisomerase inhibitor, pharmaceutical compositions comprising the same, and methods of using such combinations in the treatment of cancer.

BACKGROUND OF THE INVENTION

Generally, cancer results from the deregulation of the normal processes that control cell division, differentiation and apoptotic cell death. Apoptosis (programmed cell death) plays essential roles in embryonic development and pathogenesis of various diseases, such as degenerative neuronal diseases, cardiovascular diseases and cancer. One of the most commonly studied pathways, which involves kinase regulation of apoptosis, is cellular signaling from growth factor receptors at the cell surface to the nucleus (Crews and Erikson, Cell, 74:215-17, 1993).

The process of angiogenesis is the development of new blood vessels from the pre-existing vasculature. Angiogenesis is defined herein as involving: (i) activation of endothelial cells; (ii) increased vascular permeability; (iii) subsequent dissolution of the basement membrane and extravasation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vi) deposition of basement membrane and recruitment of perivascular cells to newly formed vessels. Normal angiogenesis is active during tissue growth from embryonic development through maturity and then enters a period of relative quiescence during adulthood. Normal angiogenesis is also activated during wound healing, and at certain stages of the female reproductive cycle. Inappropriate or pathological angiogenesis has been associated with several disease states including various retinopathies, ischemic disease, atherosclerosis, chronic inflammatory disorders, and cancer. The role of angiogenesis in disease states is discussed, for instance, in Fan et al., Trends in Pharmacol. Sci. 16:54-66; Shawver et al., DDT Vol. 2, No. 2 Feb. 1997; Folkmann, 1995, Nature Medicine 1:27-31.

In cancer the growth of solid tumors has been shown to be dependent on angiogenesis. The progression of leukemias as well as the accumulation of fluid associated with malignant ascites and pleural effusions also involve pro-angiogenic factors. (See Folkmann, J., J. Nat'l. Cancer Inst, 1990, 82, 4-6).

Central to the process of angiogenesis are vascular endothelial growth factor (VEGF) and its receptors, termed vascular endothelial growth factor receptor(s) (VEGFRs). The roles VEGF and VEGFRs play in the vascularization of solid tumors, progression of hematopoietic cancers and modulation of vascular permeability have drawn great interest in the scientific community. VEGF is a polypeptide, which has been linked to inappropriate or pathological angiogenesis (Pinedo, H. M. et al. The Oncologist, Vol. 5, No. 90001, 1-2, Apr. 2000). VEGFR(s) are protein tyrosine kinases (PTKs) that catalyze the phosphorylation of specific tyrosine residues in proteins that are involved in the regulation of cell growth, differentiation, and survival. (A. F. Wilks, Progress in Growth Factor Research, 1990, 2, 97-111; S. A. Courtneidge, Dev. Supp. 1, 1993, 57-64; J. A. Cooper, Semin. Cell Biol., 1994, 5(6),377-387; R. F. Paulson, Semin. Immunol. 1995, 7(4), 267-277; A. C. Chan, Curr. Opin. Immunol. 1996, 8(3), 394-401).

Three PTK receptors for VEGF have been identified: VEGFR1 (Flt-I); VEGFR2 (Flk-I and KDR) and VEGFR3 (Flt-4). These receptors are involved in angiogenesis and participate in signal transduction. (Mustonen, T. et al. J. Cell. Biol. 1995: 129:895-898; Ferrara and Davis-Smyth, Endocrine Reviews, 18(1):4-25, 1997; McMahon, G., The Oncologist, Vol. 5, No 90001, 3-10, Apr. 2000).

Of particular interest is VEGFR2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimulus is hypoxia, where VEGF expression is upregulated in both tumor and associated host tissues. The VEGF ligand activates VEGFR2 by binding to its extracellular VEGF binding site. This leads to receptor dimerization of VEGFRs and autophosphorylation of tyrosine residues at the intracellular kinase domain of VEGFR2. The kinase domain operates to transfer a phosphate from ATP to the tyrosine residues, thus providing binding sites for signaling proteins downstream of VEGFR-2 leading ultimately to angiogenesis. (Ferrara and Davis-Smyth, Endocrine Reviews, 18(1):4-25, 1997; McMahon, G. The Oncologist, Vol. 5, No. 90001, 3-10, Apr. 2000.)

Consequently, antagonism of the VEGFR2 kinase domain would block phosphorylation of tyrosine residues and serve to disrupt initiation of angiogenesis. Specifically, inhibition at the ATP binding site of the VEGFR2 kinase domain would prevent binding of ATP and prevent phosphorylation of tyrosine residues. Such disruption of the proangiogenesis signal transduction pathway associated with VEGFR2 should therefore inhibit tumor angiogenesis and thereby provide a potent treatment for cancer or other disorders associated with inappropriate angiogenesis. Votrient (pazopanib hydrochloride) is a multi-tyrosine kinase inhibitor of vascular endothelial growth factor receptor (VEGFR)-1, VEGFR-2, VEGFR-3, platelet-derived growth factor receptor (PDGFR)-α and -β, fibroblast growth factor receptor (FGFR)-1 and -3, cytokine receptor (Kit), interleukin-2 receptor inducible T-cell kinase (Itk), leukocyte-specific protein tyrosine kinase (Lck), and transmembrane glycoprotein receptor tyrosine kinase (c-Fms) and is approved in the US for the treatment of patients with advanced renal cell carcinoma. The chemical name of pazopanib hydrochloride is 5-[[4-[(2,3-dimethyl-2H-indazol-6-yl)methylamino]-2-pyrimidinyl]amino]-2-methylbenzenesulfonamide monohydrochloride.

The structure of the DNA helix within eukaryotic cells imposes certain topological problems that the cellular apparatus must solve in order to use its genetic material as a template. The separation of the DNA strands is fundamental to cellular processes such as DNA replication and transcription. Since eukaryotic DNA is organized into chromatin by chromosomal proteins, the ends are constrained and the strands cannot unwind without the aid of enzymes that alter topology. It has long been recognized that the advancement of the transcription or replication complex along the DNA helix would be facilitated by a swivel point which would relieve the torsional strain generated during these processes. Topoisomerases are enzymes that are capable of altering DNA topology in eukaryotic cells. They are critical for important cellular functions and cell proliferation.

There are two classes of topoisomerases in eukaryotic cells, type I and type II. Topoisomerase I is a monomeric enzyme of approximately 100,000 molecular weight. The enzyme binds to DNA and introduces a transient single strand break, unwinds the double helix (or allows it to unwind), and subsequently reseals the break before dissociating from the DNA strand. Topoisomerase II consists of two identical subunits of molecular weight 170,000. Topoisomerase II transiently breaks both strands of the helix and passes another double-strand segment through the break. Camptothecin is a water-insoluble, cytotoxic alkaloid produced by *Camptotheca accuminata* trees indigenous to China and *Nothapodytes foetida* trees indigenous to India. Camptothecin and a few close congeners thereof are the only class of compounds known to inhibit topoisomerase I. Inhibition of topoisomerase II is the major target of important commercial oncolytic agents (e.g., etoposide, doxorubicin and mitoxantrone) as well as other oncolytic agents still undergoing development.

Camptothecin (and its known congeners) have no effect on topoisomerase II and none of the known topoisomerase II inhibitors has any significant effect on topoisomerase I. Hycamtin® (topotecan hydrochloride) is a semi-synthetic derivative of campotothecin that exhibits topoisomerase I-inhibitory activity. Hycamtin® is approved in the US for the treatment of relapsed small cell lung cancer, ovarian cancer and cervical cancer. The chemical name for topotecan hydrochloride is (S)-10-[(dimethylamino)methyl]-4-ethyl-4,9-dihydroxy-1H-pyrano[3',4':6,7]indolizino[1,2-b]quinoline-3,14-(4H,12H)-dione monohydrochloride.

It would be useful to provide a novel therapy which provides more effective and/or enhanced treatment of an individual suffering the effects of cancer.

SUMMARY OF THE INVENTION

One embodiment of this invention provides a combination that includes:
(i) a compound of Structure (I):

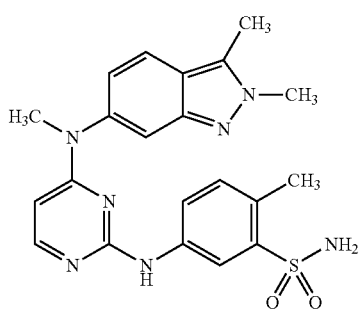

or a pharmaceutically acceptable salt thereof; and (ii) a compound of Structure (II):

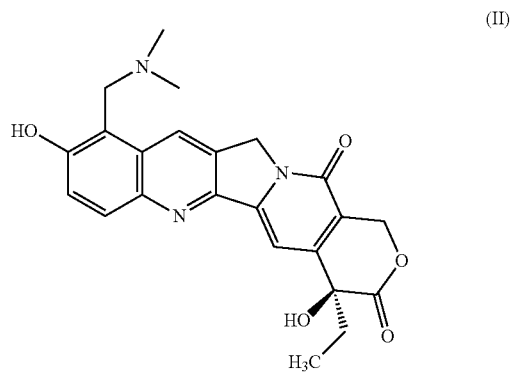 [SMILES: CC[C@@]1(O)C(=O)OCc2c1cc1n(c2=O)Cc2cc3c(CN(C)C)c(O)ccc3nc2-1]

or a pharmaceutically acceptable salt thereof.

One embodiment of this invention provides a method of treating neuroblastoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H, 12H)-dione, or a pharmaceutically acceptable salt, suitably the hydrochloride salt, thereof, to such human.

One embodiment of this invention provides a method of treating neuroblastoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H, 12H)-dione, or a pharmaceutically acceptable salt, suitably the hydrochloride salt, thereof, to such human, wherein the combination is administered within a specified period, and wherein the combination is administered for a duration of time.

One embodiment of this invention provides a method of treating neuroblastoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H, 12H)-dione, or a pharmaceutically acceptable salt, suitably the hydrochloride salt, thereof, to such human, wherein the compounds of the combination are administered sequentially.

One embodiment of this invention provides a method of treating osteosarcoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to such human.

One embodiment of this invention provides a method of treating osteosarcoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to such human, wherein the combination is administered within a specified period, and wherein the combination is administered for a duration of time.

One embodiment of this invention provides a method of treating osteosarcoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to such human, wherein the compounds of the combination are administered sequentially.

One embodiment of this invention provides a method of treating rhyabdomyosarcoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to such human.

One embodiment of this invention provides a method of treating rhabdomyosarcoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to such human, wherein the combination is administered within a specified period, and wherein the combination is administered for a duration of time.

One embodiment of this invention provides a method of treating rhabdomyosarcoma in a human in need thereof which comprises the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to such human, wherein the compounds of the combination are administered sequentially.

BRIEF DESCRIPTION OF THE DRAWINGS

FIG. 12 illustrates slides stained for the immunohistochemical examination of HIF-1 alpha, below which lies the comparison of pixel counts shown as a histogram in which * and ** represent P values below 0.05 and 0.005, respectively, compared to the control;

FIG. 13 illustrates slides stained for the immunohistochemical examination of HIF-2 alpha, below which lies the comparison of pixel counts shown as a histogram;

FIG. 14 illustrates slides stained for the immunohistochemical examination of Oct-4, below which lies the comparison of pixel counts shown as a histogram in which * and ** represent P values below 0.05 and 0.005, respectively, compared to the control;

FIG. 21 illustrates the plasma concentration-time profile of pazopanib in the single agent group (PZ) (top graph) and the plasma concentration-time profile of pazopanib in the combination group (TP+PZ) group (bottom graph), where $C_t$ is peak plasma concentration and $C_t$ is trough plasma concentration;

FIG. 23A illustrates the in vitro dose-response curves of topotecan on rhabdomyosarcoma cell lines (RD and RH30) after 72 h treatment;

DETAILED DESCRIPTION OF THE INVENTION

Figure 1:
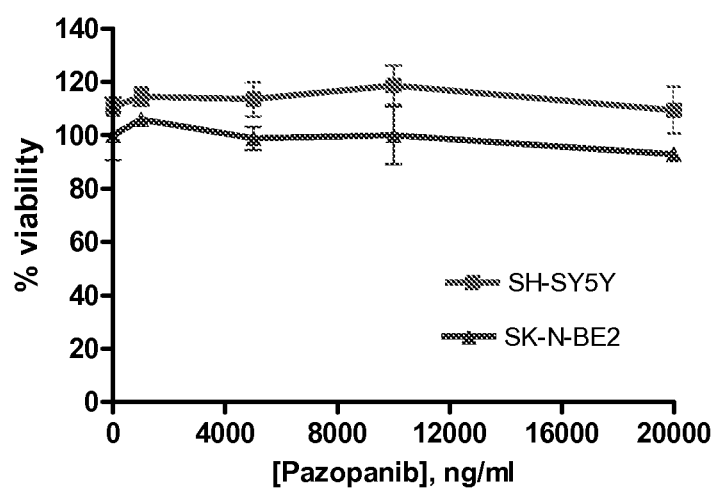
FIG. 1 Illustrates the in vitro efficacy of pazopanib on NB cell lines SH-SY5Y and SK-N-BE2.

The present invention relates to combinations that exhibit antitumor activity. Suitably, the method relates to methods of treating neuroblastoma by the co-administration of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof, (hereinafter Compound A, or a pharmaceutically acceptable salt, suitably the monohydrochloride salt, thereof), which compound is represented by Structure I:

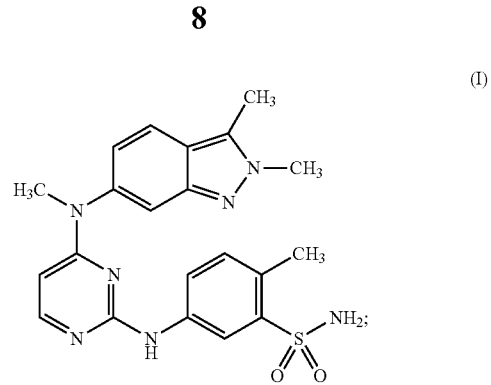

and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, (hereinafter Compound B or a pharmaceutically acceptable salt, suitably the hydrochloride salt, thereof), which compound is represented by Structure II:

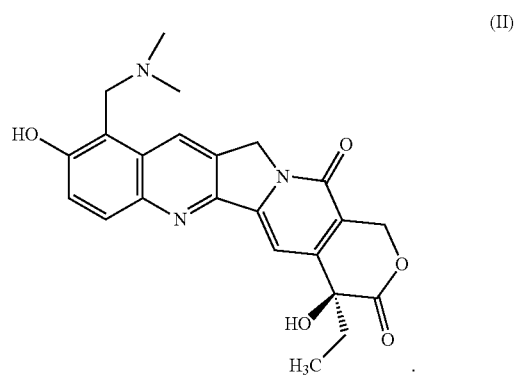 [SMILES: CC[C@@]1(O)C(=O)OCc2c1cc1n(c2=O)Cc2cc3c(CN(C)C)c(O)ccc3nc2-1]

Compound A is disclosed and claimed, along with pharmaceutically acceptable salts thereof, as being useful as an inhibitor of VEGFR activity, particularly in treatment of cancer, in International Application No. PCT/US01/49367, having an International filing date of Dec. 19, 2001, International Publication Number WO02/059110 and an International Publication date of Aug. 1, 2002, the entire disclosure of which is hereby incorporated by reference, Compound A is the compound of Example 69. Compound A can be prepared as described in International Application No. PCT/US01/49367.

Suitably, Compound A is in the form of a monohydrochloride salt. This salt form can be prepared by one of skill in the art from the description in International Application No. PCT/US01/49367, having an International filing date of Dec. 19, 2001.

Compound A is sold commercially as the monohydrochloride salt. Compound A is known by the generic name pazopanib and the trade name Votrient®.

Compound B is disclosed and claimed, along with pharmaceutically acceptable salts thereof, as being useful as an inhibitor of topoisomerase I, particularly in treatment of cancer, in U.S. Pat. No. 5,004,758, having a filing date of Nov. 2, 1988, the entire disclosure of which is hereby incorporated by reference, Compound B is compound IS (as the acetate salt). Compound B can be prepared as described in U.S. Pat. No. 5,734,056.

Suitably, Compound B is in the form of a hydrochloride salt. The salt form can be prepared by one of skill in the art from the description in U.S. Pat. No. 5,004,758 and/or by methods that will be readily apparent to those skilled in the art.

Compound B is sold commercially as the monohydrochloride salt. Compound B is known by the generic name topotecan and the trade name Hycamtin®.

The administration of a therapeutically effective amount of the combinations of the invention are advantageous over the individual component compounds in that the combinations will provide one or more of the following improved properties when compared to the individual administration of a therapeutically effective amount of a component compound: i) a greater anticancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or yl) an increase in the bioavailability of one or both of the component compounds.

The compounds of the invention may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of Compound A, and pharmaceutically acceptable salts thereof, and Compound B, and pharmaceutically acceptable salts thereof.

The compounds of the invention may form a solvate which is understood to be a complex of variable stoichiometry formed by a solute (in this invention, Compound A or a salt thereof and/or Compound B or a salt thereof) and a solvent. Such solvents for the purpose of the invention may not interfere with the biological activity of the solute. Examples of suitable solvents include, but are not limited to, water, methanol, ethanol and acetic acid. Suitably the solvent used is a pharmaceutically acceptable solvent. Suitably the solvent used is water.

The pharmaceutically acceptable salts of the compounds of the invention are readily prepared by those of skill in the art.

Also, contemplated herein is a method of treating neuroblastoma using a combination of the invention where Compound A, or a pharmaceutically acceptable salt thereof, and/or Compound B or a pharmaceutically acceptable salt thereof are administered as pro-drugs.

Also, contemplated herein is a method of treating osteosarcoma using a combination of the invention where Compound A, or a pharmaceutically acceptable salt thereof, and/or Compound B or a pharmaceutically acceptable salt thereof are administered as pro-drugs.

Also, contemplated herein is a method of treating rhabdomyosarcoma using a combination of the invention where Compound A, or a pharmaceutically acceptable salt thereof, and/or Compound B or a pharmaceutically acceptable salt thereof are administered as pro-drugs.

Pharmaceutically acceptable pro-drugs of the compounds of the invention are readily prepared by those of skill in the art.

When referring to a dosing protocol, the term "day", "per day" and the like, refer to a time within one calendar day which begins at midnight and ends at the following midnight.

By the term "treating" and derivatives thereof as used herein, is meant therapeutic therapy. In reference to a particular condition, treating means: (1) to ameliorate the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition.

Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. In aspects of the invention relating to neuroblastoma, prophylactic therapy is appropriate, for example, when a subject is considered at high risk for developing neuroblastoma, such as when a subject has a strong family history of neuroblastoma. In aspects of the invention relating to osteosarcoma, prophylactic therapy is appropriate, for example, when a subject is considered at high risk for developing osteosarcoma, such as when a subject has a strong family history of osteosarcoma. In aspects of the invention relating to rhabdomyosarcoma, prophylactic therapy is appropriate, for example, when a subject is considered at high risk for developing rhabdomyosarcoma, such as when a subject has a strong family history of rhabdomyosarcoma.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

By the term "combination" and derivatives thereof, as used herein is meant either, simultaneous administration or any manner of separate sequential administration of a therapeutically effective amount of Compound A, or a pharmaceutically acceptable salt thereof, and Compound B or a pharmaceutically acceptable salt thereof. Preferably, if the administration is not simultaneous, the compounds are administered in a close time proximity to each other. Furthermore, it does not matter if the compounds are administered in the same dosage form, e.g. one compound may be administered topically and the other compound may be administered orally. Suitably, both compounds are administered orally.

By the term "combination kit" as used herein is meant the pharmaceutical composition or compositions that are used to administer Compound A, or a pharmaceutically acceptable salt thereof, and Compound B, or a pharmaceutically acceptable salt thereof, according to the invention. When both compounds are administered simultaneously, the combination kit can contain Compound A, or a pharmaceutically acceptable salt thereof, and Compound B, or a pharmaceutically acceptable salt thereof, in a single pharmaceutical composition, such as a tablet, or in separate pharmaceutical compositions. When the compounds are not administered simultaneously, the combination kit will contain Compound A, or a pharmaceutically acceptable salt thereof, and Compound B, or a pharmaceutically acceptable salt thereof, in separate pharmaceutical compositions. The combination kit can comprise Compound A, or a pharmaceutically acceptable salt thereof, and Compound B, or a pharmaceutically acceptable salt thereof, in separate pharmaceutical compositions in a single package or in separate pharmaceutical compositions in separate packages.

In one aspect there is provided a combination kit comprising the components: Compound A, or a pharmaceutically acceptable salt thereof, in association with a pharmaceutically acceptable carrier; and Compound B, or a pharmaceutically acceptable salt thereof, in association with a pharmaceutically acceptable carrier.

In one embodiment of the invention the combination kit comprises the following components: Compound A, or a pharmaceutically acceptable salt thereof, in association with a pharmaceutically acceptable carrier; and Compound B, or a pharmaceutically acceptable salt thereof, in association with a pharmaceutically acceptable carrier, wherein the components are provided in a form which is suitable for sequential, separate and/or simultaneous administration.

In one embodiment the combination kit comprises: a first container comprising Compound A, or a pharmaceutically acceptable salt thereof, in association with a pharmaceutically acceptable carrier; and a second container comprising Compound B, or a pharmaceutically acceptable salt thereof, in association with a pharmaceutically acceptable carrier, and a container means for containing said first and second containers.

The "combination kit" can also be provided by instruction, such as dosage and administration instructions. Such dosage and administration instructions can be of the kind that is provided to a doctor, for example by a drug product label, or they can be of the kind that is provided by a doctor, such as instructions to a patient.

As used herein the term "Compound $A^2$" means—Compound A, or a pharmaceutically acceptable salt thereof—.

As used herein the term "Compound $B^2$" means—Compound B, or a pharmaceutically acceptable salt thereof—.

In some embodiments according to the present invention, the combinations of this invention are administered within a "specified period".

By the term "specified period" and derivatives thereof, as used herein is meant the interval of time between the administration of one of Compound $A^2$ and Compound $B^2$ and the other of Compound $A^2$ and Compound $B^2$. Unless otherwise defined, the specified period can include simultaneous administration. When both compounds of the invention are administered once a day the specified period refers to timing of the administration of Compound $A^2$ and Compound $B^2$ during a single day. When one or both compounds of the invention are administered more than once a day, the specified period is calculated based on the first administration of each compound on a specific day. All administrations of a compound of the invention that are subsequent to the first during a specific day are not considered when calculating the specific period.

The specified period can be various time periods. For example, Compound $A^2$ and Compound $B^2$ can be administered within about 24, 23, 22, 21, 20, 19, 18, 17, 16, 15, 14, 13, 12, 11, 10, 9, 8, 7, 6, 5, 4, 3, 2 or 1 hours of each other, in which case the specified period will be about 24, 23, 22, 21, 20, 19, 18, 17, 16, 15, 14, 13, 12, 11, 10, 9, 8, 7, 6, 5, 4, 3, 2 or 1 hours, respectively. As used herein, the administration of Compound $A^2$ and Compound $B^2$ in less than about 45 minutes apart is considered simultaneous administration.

Suitably, when the combination of the invention is administered for a "specified period," the compounds will be co-administered for a "duration of time."

By the term "duration of time" and derivatives thereof, as used herein is meant that both compounds of the invention are administered within a "specified period" for an indicated number of consecutive days, optionally followed by a number of consecutive days where only one of the component compounds is administered. Unless otherwise defined, the "duration of time" and in all dosing protocols described herein, do not have to commence with the start of treatment and terminate with the end of treatment, it is only required that the number of consecutive days in which both compounds are administered and the optional number of consecutive days in which only one of the component compounds is administered, or the indicated dosing protocol, occur at some point during the course of treatment.

The duration of time can be various time periods. For example, Compound $A^2$ and Compound $B^2$ can both be administered within a specified period for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days during the course of treatment, in which case the duration of time will be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, respectively. When, during the course of treatment, both compounds are administered within a specified period for over 30 consecutive days, the treatment is considered chronic treatment and will continue until an altering event, such as a reassessment in neuroblastoma, osteosarcoma, or rhabdomyosarcoma status as the case may be or a change in the condition of the patient, warrants a modification to the protocol.

Various treatment protocols are contemplated in embodiments of the present invention. For example, Compound $A^2$ and $B^2$ can be co-administered within a specified period for at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days, followed by the administration of Compound $A^2$ alone for at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days, in which case the duration of time will be at least the number of consecutive days that Compound $A^2$ and Compound $B^2$ are both administered plus the number of consecutive days of administration of Compound $A^2$ alone (e.g., if Compound $A^2$ and Compound $B^2$ are both administered for 6 consecutive days followed by administration of Compound $A^2$ alone for 8 consecutive days, the duration of time will be at least 14 consecutive days).

In other embodiments, Compound $A^2$ and Compound $B^2$ are both administered within a specified period for a number of consecutive days during a certain time period, and compound $A^2$ is administered during the other days of the certain time period. In some embodiments, the certain time period is n=2, 3, 4, 5, 6, 7, 8, 9, 10, 11, 12, 13, 14, 15, 16, 17, 18, 19, 20, 21, 22, 23, 24, 25, 26, 27, 28, 29 or 30 days, the days of consecutive administration of Compound $A^2$ and Compound $B^2$ within a specified time period is m=1, 2, 3, 4, 5, 6, 7, 8, 9, 10, 11, 12, 13, 14, 15, 16, 17, 18, 19, 20, 21, 22, 23, 24, 25, 26, 27, 28 or 29, and the days of administration of Compound $A^2$ is n−m, where n−m is at least 1. For example, Compound $A^2$ and Compound $B^2$ can be administered within a specified time period for 1, 2, 3, 4, 5, 6, 7, 8, 9, 10, 11, 12 or 13 consecutive days over a certain time period of 14 days, during which Compound $A^2$ is administered for the other 13, 12, 11, 10, 9, 8, 7, 6, 5, 4, 3, 2 or 1 days, respectively. In this example, n=14, m=1, 2, 3, 4, 5, 6, 7, 8, 9, 10, 11, 12 or 13, and n−m=13, 12, 11, 10, 9, 8, 7, 6, 5, 4, 3, 2 or 1, respectively. The consecutive days during which Compound $A^2$ and Compound $B^2$ are both administered within a specified time period can occur any time during the certain time period. Accordingly, in the foregoing example, Compound $A^2$ could be administered alone for 4 consecutive days follow by administration of both Compound $A^2$ and Compound $B^2$ for 5 consecutive days, followed by administering Compound $A^2$ alone for 5 consecutive days to complete the 14 day certain time period.

While treatment protocols have been described with respect to administration of both Compound $A^2$ and Compound $B^2$ within a specified period in conjunction with administration of Compound $A^2$ alone, embodiments of the present invention also include similar treatment protocols in which Compound $A^2$ and Compound $B^2$ are both administered within a specified period in conjunction with administration of Compound $B^2$ alone.

Other embodiments of the present invention include administration of both Compound $A^2$ and Compound $B^2$ within a specified period in conjunction with administration of Compound $A^2$ alone and administration of Compound $B^2$ alone. For example, in some embodiments Compound $A^2$ and Compound $B^2$ are both administered within a specified period for a number of consecutive days during a certain time period, Compound $A^2$ is administered alone during a number of days during the certain time period, and Compound $B^2$ is administered alone during the other days during the certain time period. In some embodiments, the certain time period is n=3, 4, 5, 6, 7, 8, 9, 10, 11, 12, 13, 14, 15, 16, 17, 18, 19, 20, 21, 22, 23, 24, 25, 26, 27, 28, 29 or 30 days, the days of consecutive administration of Compound $A^2$ and Compound $B^2$ within a specified time period is m=1, 2, 3, 4, 5, 6, 7, 8, 9, 10, 11, 12, 13, 14, 15, 16, 17, 18, 19, 20, 21, 22, 23, 24, 25, 26, 27 or 28, the days of administration of Compound $A^2$ during the certain time period is p=1, 2, 3, 4, 5, 6, 7, 8, 9, 10, 11, 12, 13, 14, 15, 16, 17, 18, 19, 20, 21, 22, 23, 24, 25, 26, 27 or 28, and the days of administration of Compound $B^2$ is n–m–p, where n–m–p is at least 1. For example, Compound $A^2$ and Compound $B^2$ can both be administered within a specified time period for 1, 2, 3, 4, 5, 6, 7, 8, 9, 10, 11 or 12 consecutive days over a certain time period of 14 days, during which Compound $A^2$ is administered for 1, 2, 3, 4, 5, 6, 7, 8, 9, 10, 11 or 12 days, and Compound $B^2$ is administered for 1, 2, 3, 4, 5, 6, 7, 8, 9, 10, 11 or 12 days. In this example, n=14, m=1, 2, 3, 4, 5, 6, 7, 8, 9, 10, 11 or 12, p=1, 2, 3, 4, 5, 6, 7, 8, 9, 10, 11 or 12, and n–m–p=1, 2, 3, 4, 5, 6, 7, 8, 9, 10, 11 or 12. The consecutive days during which Compound $A^2$ and Compound $B^2$ are both administered within a specified time period can occur any time during the certain time period. Accordingly, in the foregoing example, Compound $A^2$ could be administered alone for 4 consecutive days follow by administration of both Compound $A^2$ and Compound $B^2$ for 5 consecutive days, followed by administering Compound $B^2$ alone for 5 consecutive days to complete the 14 day certain time period. Administration of Compound $A^2$ alone and administration of Compound $B^2$ alone do not have to occur on consecutive days. Accordingly, in the foregoing example, Compound $A^2$ could be administered for 2 consecutive days, followed by administration of Compound $B^2$ for 1 day followed by administration of both Compound $A^2$ and Compound $B^2$ for 5 consecutive days, followed by administration of Compound $A^2$ for 1 day, followed by administration of Compound $B^2$ for 5 consecutive days.

If the compounds are not administered during a "specified period", they are administered sequentially. By the term "sequential administration", and derivatives thereof, as used herein is meant that one of Compound $A^2$ and Compound $B^2$ is administered for one or more consecutive days and the other of Compound $A^2$ and Compound $B^2$ is subsequently administered for one or more consecutive days. Also, contemplated herein is a drug holiday utilized between the sequential administration of one of Compound $A^2$ and Compound $B^2$ and the other of Compound $A^2$ and Compound $B^2$. As used herein, a drug holiday is a period of one or more days after the administration of one of Compound $A^2$ and Compound $B^2$ and before the sequential administration of the other of Compound $A^2$ and Compound $B^2$ where neither Compound $A^2$ nor Compound $B^2$ is administered. The drug holiday can be a various number of days. In some embodiments, the drug holiday is 1, 2, 3, 4, 5, 6, 7, 8, 9, 10, 11, 12, 13 or 14 days.

In some embodiments, one of Compound $A^2$ and Compound $B^2$ is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 consecutive days, followed by an optional drug holiday of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days, followed by administration of the other of Compound $A^2$ and Compound $B^2$ for 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 consecutive days.

It is understood that a "specified period" administration and a "sequential" administration can be followed by repeat dosing or can be followed by an alternate dosing protocol, and a drug holiday may precede the repeat dosing or alternate dosing protocol.

It is to be understood that the treatment protocols and regimens described herein can comprise the entire treatment protocol for a given patient or, alternatively, can comprise only a portion of the entire treatment protocol for the patient.

Suitably, the amount of Compound $A^2$ administered as part of the combination according to the present invention will be an amount selected from a lower limit of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 or 300 mg to an upper limit of about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, or 800 mg. It is to be understood that embodiments of the present invention include any number in the ranges listed above. In some embodiments, the selected amount of Compound $A^2$ is administered from 1, 2, 3, 4, 5, or 6 times a day.

Suitably, the amount of Compound $B^2$ administered as part of the combination according to the present invention will be an amount selected from a lower limit of about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95 or 2.0 mg to an upper limit of about 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.0, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95 or 4.0 mg. In some embodiments, the selected amount of Compound $B^2$ is administered 1, 2, 3, 4, 5 or 6 times a day.

As used herein, all amounts specified for Compound $A^2$ and Compound $B^2$ are indicated as the administered amount of free or unsalted compound per dose.

In aspects relating to treatment of neuroblastoma, the methods of the present invention may also be employed with other therapeutic methods of neuroblastoma treatment. In aspects relating to treatment of osteosarcoma, the methods of the present invention may also be employed with other therapeutic methods of osteosarcoma treatment. In aspects relating to treatment of rhabdomyosarcoma, the methods of the present invention may also be employed with other therapeutic methods of rhabdomyosarcoma treatment.

While it is possible that, for use in therapy, therapeutically effective amounts of the combinations of the present invention may be administered as the raw chemical, it is preferable to present the combinations as a pharmaceutical composition or compositions. Accordingly, the invention further provides pharmaceutical compositions, which include Compound $A^2$ and/or Compound $B^2$ and one or more pharmaceutically acceptable carriers. The combinations of the present invention are as described above. The carrier(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical formulation including admixing Compound $A^2$ and/or Compound $B^2$ with one or more pharmaceutically acceptable carriers. As indicated above, such elements of the pharmaceutical combination utilized may be presented in separate pharmaceutical compositions or formulated together in one pharmaceutical formulation.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

Compound $A^2$ and Compound $B^2$ may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It will be appreciated that the preferred route may vary with, for example, the condition of the recipient of the combination and the precise nature of the neuroblastoma, osteosarcoma, or rhabdomyosarcoma to be treated. It will also be appreciated that each of the agents administered may be administered by the same or different routes and that Compound $A^2$ and Compound $B^2$ may be compounded together in a pharmaceutical composition/formulation. In some embodiments, Compound $A^2$ and Compound $B^2$ are administered in separate pharmaceutical compositions. In other embodiments, Compound $A^2$ and Compound $B^2$ are administered in fixed-dose pharmaceutical compositions that include both Compound $A^2$ and Compound $B^2$.

The compounds or combinations of the current invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include a prolonged release material, such as glyceryl monostearate or glyceryl distearate, alone or with a wax. The amount of solid carrier varies widely but, suitably, may be from about 0.05 mg to about 1 g per dosage unit. When a liquid carrier is used, the preparation will suitably be in the form of a syrup, elixir, emulsion, soft gelatin capsule, sterile injectable liquid such as an ampoule, or an aqueous or nonaqueous liquid suspension.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

It should be understood that in addition to the ingredients mentioned above, the formulations may include other agents conventional in the art having regard to the type of formulation in question, for example those suitable for oral administration may include flavoring agents.

As indicated, therapeutically effective amounts of the combinations of the invention (Compound $A^2$ in combination with Compound $B^2$) are administered to a human. In some embodiments of the present invention as it relates to neuroblastoma, the human is less than 20, 19, 17, 16, 15, 14, 13, 12, 11, 10, 9, 8, 7, 6, 5, 4, 3, 2 or 1 years old. Typically, the therapeutically effective amount of the administered agents of the present invention will depend upon a number of factors including, for example, the age and weight of the subject, the precise condition requiring treatment, the severity of the condition, the nature of the formulation, and the route of administration. Ultimately, the therapeutically effective amount will be at the discretion of the attending physician.

This invention provides a combination comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof.

This invention also provides for a combination comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, for use in the treatment of neuroblastoma.

This invention also provides a pharmaceutical composition comprising a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof.

This invention also provides a combination kit comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof.

This invention also provides for the use of a combination comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, in the manufacture of a medicament for the treatment of neuroblastoma.

This invention also provides a method of treating neuroblastoma which comprises administering a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to a subject in need thereof.

This invention also provides for a combination comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, for use in the treatment of osteosarcoma.

This invention also provides for the use of a combination comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, in the manufacture of a medicament for the treatment of osteosarcoma.

This invention also provides a method of treating osteosarcoma which comprises administering a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to a subject in need thereof.

This invention also provides for a combination comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, for use in the treatment of rhabdomyosarcoma.

This invention also provides for the use of a combination comprising 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, in the manufacture of a medicament for the treatment of rhabdomyosarcoma.

This invention also provides a method of treating rhabdomyosarcoma which comprises administering a combination of 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt, thereof and (S)-10-[(dimethylamino)methyl]-4-ethyl-4,9-dihydroxy-1H-pyrano[3',4':6,7]indolizino[1,2-b]quinoline-3,14-(4H,12H)-dione, or a pharmaceutically acceptable salt, suitably the hydrochloride salt, thereof, to a subject in need thereof.

The following examples are intended for illustration only and are not intended to limit the scope of the invention in any way.

EXPERIMENTAL DETAILS

Neuroblastoma
Materials and Methods:
Drugs and Reagents:

Topotecan hydrochloride, (S)-10-[(dimethylamino)methyl]-4-ethyl-4,9-dihydroxy-1H-yrano[3',4':6,7]indolizino[1,2-b]quinoline-3,14(4H,12H)-dione monohydrochloride and pazopanib monohydrochloride, (5-[[4-[(2,3-Dimethyl-2H-indazol-6-yl)methylamino]-2-pyrimidinyl]amino]-2-methylbenzolsulfonamide are available from GlaxoSmithkline. Topotecan-d6 was purchased from Toronto Research Chemicals (catalogue #T542502).

Cell Lines:

SK-N-BE(2) (MYCN amplified) and SH-SY5Y (non-MYCN amplified neuroblastoma cell lines) were obtained from American Type Culture Collection (ATCC) (Manassas, Va.); BE(2)-c sub-clone of SK-N-BE(2) was obtained from Dr. Michelle Haber (Children's Cancer Institute for Medical Research, Lowry Cancer Research Centre, Randwick, Australia); Human Umbilical Vein Endothelial Cells (HUVECs) were obtained from Dr. Herman Yeger (The Hospital for Sick Children, Toronto, Ontario, Canada) and Tumor Initiating (TIC) cell lines NB12 and NB88, were obtained from Dr. David Kaplan (The Hospital for Sick Children, Toronto, Ontario, Canada). TICs NB12 and NB88 were isolated from the bone marrow metastases of relapsed high-risk neuroblastoma patients. Neuroblastoma cell lines SK-N-BE(2) and SH-SY5Y were grown in alpha-MEM containing 10% fetal bovine serum and 1% antibiotic mixture in humidified atmosphere at 37° C. with 5% $CO_2$. NB12 and NB 88 were cultured as described previously.

In-vitro Cytotoxicity:

50,000 cells were seeded in 48 well plates and incubated for 48 h, after which they were treated with topotecan and/or pazopanib for 72 h. Cell viability was determined by Alamar Blue assay. Alamar blue (10% of total volume was added to each well three hours prior to fluorometric detection). Fluorometric detection was performed using the SPECTRAmax gemini Spectrophotometer at excitation wavelength of 540 nm and emission wavelength of 590 nm.

Tumor Xenograft Models:

$1 \times 10^6$ SK-N-BE(2) cells or 30,000 NB12 cells were implanted subcutaneously into the inguinal fat pad of each of non-obese diabetic/severe combined immune deficient (NOD/SCID) mice. When tumors reached 0.5 cm in diameter, the animals were randomized into four groups and treated daily by oral gavage. The animals were grouped as: Control group, 'LDM' topotecan group or 'TP' (1.0 mg/Kg topotecan), pazopanib group or 'PZ' (150 mg/Kg pazopanib), and combination group or TP+PZ (1.0 mg/Kg topotecan+150 mg/Kg pazopanib). The criteria for end point were tumor sizes exceeding 2.0 cms in diameter or animals showing signs of morbidity. The tumor sizes were measured on a daily basis until the end point or sacrifice. The long (D) and short diameters (d) were measured with calipers. Tumor volume (cm$^3$) was calculated as V=0.5×D×d$^2$. When end point was reached, the animals were sacrificed by cervical dislocation. Tumors were excised and were fixed in 10% formalin solution.

Metastatic Models:

1×10$^6$ BE(2)-c cells were injected into lateral tail veins of NOD/SCID mice to generate 'experimental' metastases. After 14 days, mice were randomized into four groups and treated in same way as the inguinal xenograft model. The treatment was continued until death or end point.

Immunohistochemistry and Histopathology:

Formalin fixed tissues were paraffin embedded and sections cut at 7 um. These paraffin embedded sections were deparaffinized through xylene and ethanol, rehydrated in Phosphate-buffered Saline (PBS) (#311-0,0-CL, Wisent Bioproducts) and incubated with primary antibodies at 4° C. The primary antibodies were anti-HIF-1 alpha (#NB100-131, Novus Biologicals, dilution 1:3000), HIF-2 alpha (#NB100-122, Novus Biologicals, dilution 1:100), Oct-4 (#2890S, Cell Signalling, dilution 1:100), von Willebrand factor (#A0082; DakoCytomation, Glostrup, Denmark). After the primary antibody treatment, all the slides were washed three times with PBS and incubated with broad spectrum poly-horse radish peroxidase (HRP) conjugate 35 secondary antibody (87-9663, Invitrogen) for 1 h at room temperature. After washing three times with PBS, slides were stained with diaminobenzidine (DAB) and counterstained with hematoxylin. Microscopic images of six fields of high vascular density were digitally captured for vWF-stained slides, while for HIF-1 alpha, HIF-2 alpha and Oct-4 stained slides, the images of six randomly selected areas were captured. The pixel values for stained areas were quantified using ImageJ software. Tumor angiogenesis was quantified as the number of pixels of regions positive for vWF.

In the metastatic model, the animals' organs (liver, kidney, adrenal, and femur) were removed after the death/sacrifice of animals, and were fixed in 10% formalin and paraffin-embedded. These paraffin-embedded sections were then stained with hematoxylin and eosin and microscopically examined.

Analysis of Circulating Endothelial Progenitor Cells (CEPs) and Circulating Endothelial Cells (CECs):

Approximately 160 µl of mouse blood was collected in K2-EDTA tubes by saphenous vein puncture from animals of the SK-N-BE(2) xenograft model (after one week treatment) and BE(2)-c metastatic model (after one week and four weeks treatment). Blood was immediately stored at 4° C. until analysis. The CEP/CECs were measured by flow cytometry within 48 hrs of blood collection as previously described. CEPs were defined as CD45−, VEGFR-2+, CD117+, and CD13+, while CECs were defined as CD45−, VEGFR-2+, CD117−, and CD13+. The absolute number of CEPs was calculated as the percentage of events collected in CEP enumeration gates multiplied by the total white blood cell (WBC) count.

Pharmacokinetics of Topotecan (TP) and Pazopanib (PZ)

Non-tumor bearing animals were randomized into four groups (n=3): Control, PZ, TP and TP+PZ. The doses of the drugs were the same as for the inguinal xenograft and metastatic models described above.

After single drug administration, the saphenous vein blood samples (30 µl) were collected in heparinized microcentrifuge tubes at 30 min, 1 h, 2 h, 4 h, 8 h, 12 h, 18 h and 24 h as per the Lab Animal Services protocol. Plasma was immediately isolated after blood collection by centrifugation. For the topotecan assay, 10 µl plasma was immediately precipitated with 20 µl methanol and centrifuged. The supernatant and rest of the plasma were stored at −80 µC until analysis.

Assay of pazopanib: 5 µl of plasma was precipitated with 40 µl methanol and centrifuged. 30 µl of supernatant was injected into the HPLC system, which consisted of Phenomenox C18 (Luna; 150×4.6 mm; particle size 5 microns) column, UV detector (267 nm). The mobile phase was 50:50 mixture of 10 mM potassium phosphate and methanol, with flow rate 1.0 ml/min. The calibration standards were 5, 10, 50, 100 and 200 µg/ml.

Assay of topotecan: Prior to analysis, the previously prepared 20 µl methanolic extract was mixed with 50 µl of internal standard solution (5 ng/ml d6 topotecan dissolved 1% formic acid in acetonitrile). The mixture was then centrifuged and the supernatant was transferred to auto-sampler vials.

The LC/MS system consisted of an HPLC (Agilent Infinity 1290), Column (Kinetex HILIC, 2.6u, 100A, 50×4.6 mm) and a mass spectrometer (Sciex 5500-QTrap). The analytes were eluted by gradient flow. Mobile phase A was water: actonitrile (10:90) and mobile phase B was 10 mM ammonium acetate (pH 3.2). The mobile phase ratio was 5% A for 0-2 min, 20% A for 4-6 min and 5% A for 8-10 min at a flow rate 0.5 ml/min. The samples were analyzed by positive ion electrospray ionization technique in multiple reaction monitoring modes. The following mass transitions were monitored: 422.2 to 377 m/z, (topotecan M+H) and 428.2 to 377 m/z (topotecan d6 M+H). The calibration standard range was 0.5 ng/ml to 10 ng/ml.

Statistical Analysis

In vitro dose-response, in vivo tumor growth curves and the number of pixels for immunohistochemistry are presented as mean±SD. Statistical significance was assessed by student's T-test and $P<0.05$ was considered to be significant.

Results:

Drug-induced in vitro Cytotoxities

Figure 2:
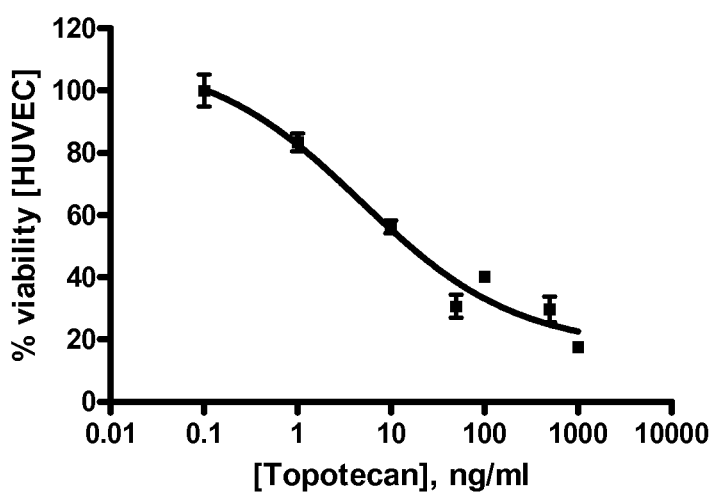
FIG. 2 Illustrates the dose response plot of topotecan on HUVEC.
Figure 3:
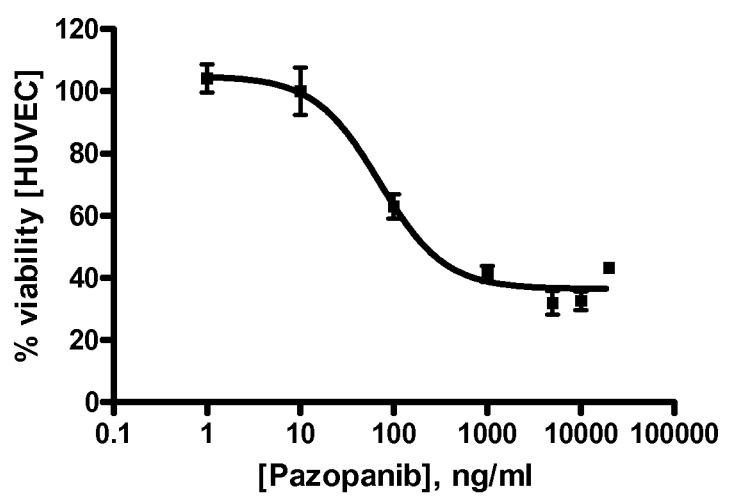
FIG. 3 Illustrates the dose response plot of pazopanib on HUVEC.
Figure 4:
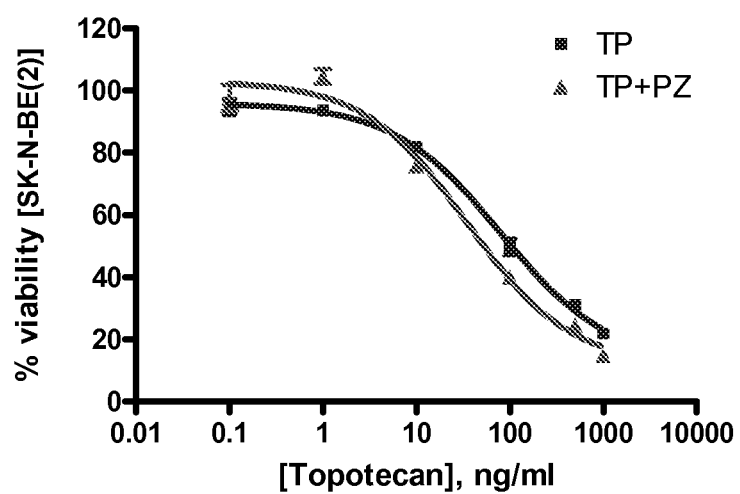
FIG. 4 Illustrates the dose-response plot of topotecan alone and in combination with 5000 ng/ml pazopanib on the SK-N-BE(2) neuroblastoma cell line.
Figure 5:
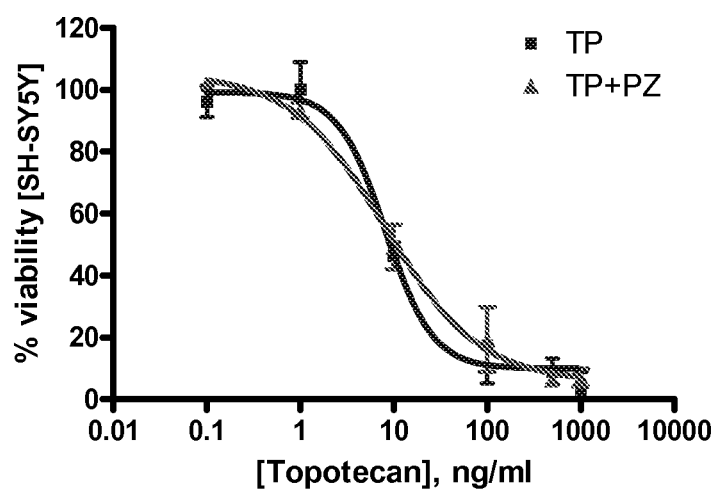
FIG. 5 Illustrates the dose-response plot of topotecan alone and in combination with 5000 ng/ml pazopanib on the SH-SY5Y neuroblastoma cell line.
Figure 6:
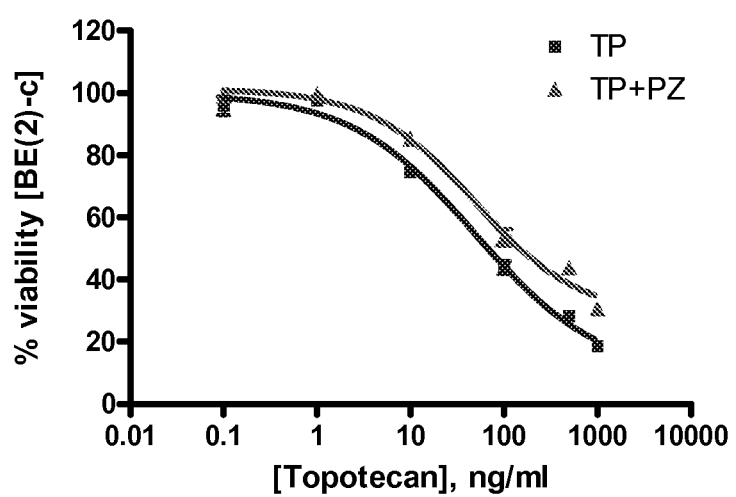
FIG. 6 Illustrates the dose-response plot of topotecan alone and in combination with 5000 ng/ml pazopanib on the BE(2)-c neuroblastoma cell line.
Figure 7:
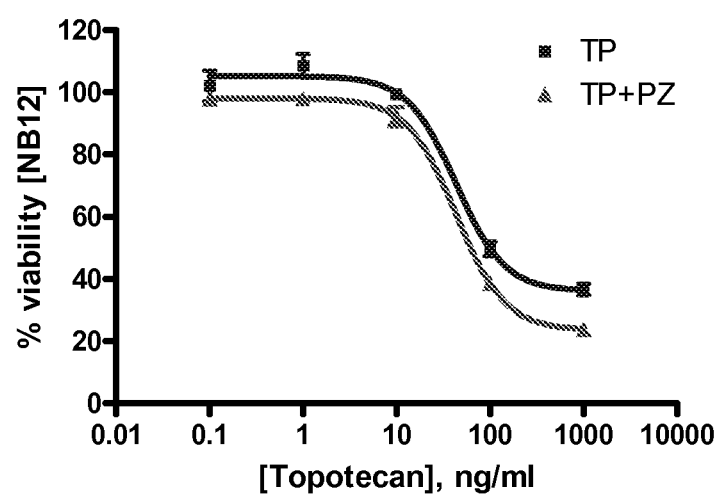
FIG. 7 Illustrates the dose-response plot of topotecan alone and in combination with 5000 ng/ml pazopanib on the NB12 neuroblastoma cell line.
Figure 8:
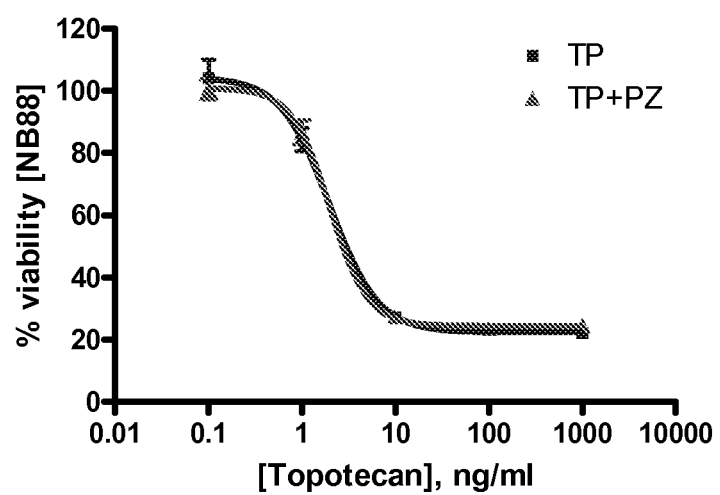
FIG. 8 Illustrates the dose-response plot of topotecan alone and in combination with 5000 ng/ml pazopanib on the NB88 cell line.

Pazopanib did not affect the viabilities of the established neuroblastoma cell lines SK-N-BE(2) or SH-SY5Y even at a high concentration of 5000 ng/ml (FIG. 1). Both topotecan and pazopanib caused a dose-dependent reduction in viability of HUVEC cells with IC50 of 4.87 ng/ml and 398 ng/ml respectively (FIGS. 2 and 3). Topotecan demonstrated a dose-dependent reduction in the viability of the neuroblastoma cell lines and patient-derived TICs (FIGS. 4 through 8). SH-SY5Y cells (IC50=5.3 ng/ml) were more sensitive to topotecan than BE(2)-c cells (IC50=45.6 ng/ml) and SK-N-BE(2) cells (IC50=65.0 ng/ml). Among TICs, NB88 (IC50=3.9 ng/ml) was considerably more sensitive to topotecan than NB12 (IC50=63.1 ng/ml). Addition of 5000 ng/ml pazopanib caused a significant reduction of IC50 only in the case of SK-N-BE(2) cells (IC50=35.12 ng/ml, P=0.046).

Impact of Metronomic TP in Combination with Pazopanib on Growth of Neuroblastoma Xenografts In the group of animals implanted with SK-N-BE(2) cells palpable tumors started appearing approximately two weeks after cell implantation and took an additional week to reach 0.5 cm in diameter, after which the treatment was started. The effect of treatment was assessed by measuring regression of tumors and by survival times. Drugs were administered daily over a period of 56 days, and the animals belonging to the TP+PZ group were also retreated from the 103$^{rd}$ day to evaluate the impact of resuming treatment on reversing drug resistance. Retreatment was continued until the 125$^{th}$ day, after which the mice were sacrificed.

Figure 9A:
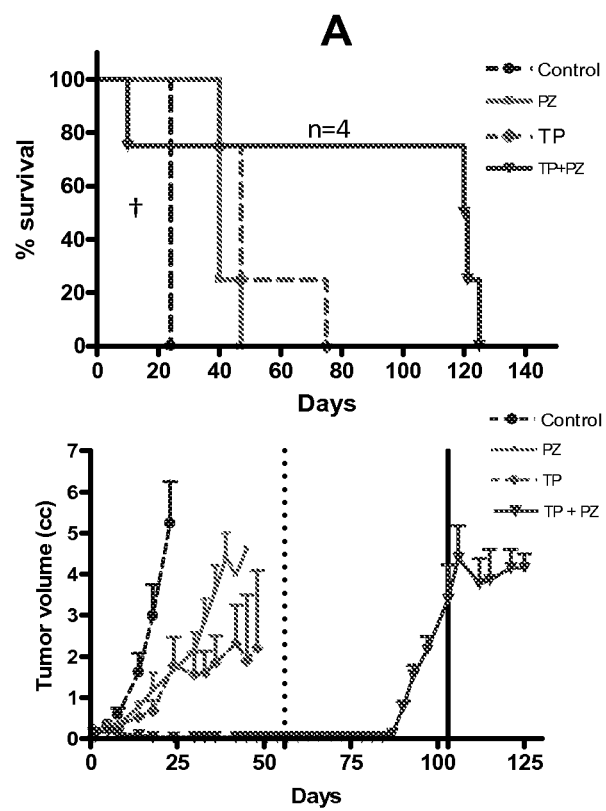
FIG. 9A illustrates a Kaplan Meier survival curve (top) and a tumor growth rate curve (bottom) for SK-N-BE(2) xenograft model, in which the dotted line indicates that the treatment was stopped after 56 days, while the solid line indicates that the animals were retreated starting from 103 days.

In the SK-N-BE(2) xenograft model, all three treatment regimens delayed tumor growth and significantly enhanced mouse survival, compared to the control untreated group (FIG. 9A). No significant difference was observed in tumor growth rate between the TP and PZ group. The TP+PZ combination significantly enhanced survival times compared to TP treatment alone. In this model, compared to control, TP, PZ significantly enhanced survival (P<0.05). The survival in the TP+PZ treated group was significantly higher compared to both control (P<0.005) and the single agents' groups (P<0.005).

Retreatment was associated by transient tumor growth delay up to 125 days when tumor regrew and animals were sacrificed.

Figure 9B:
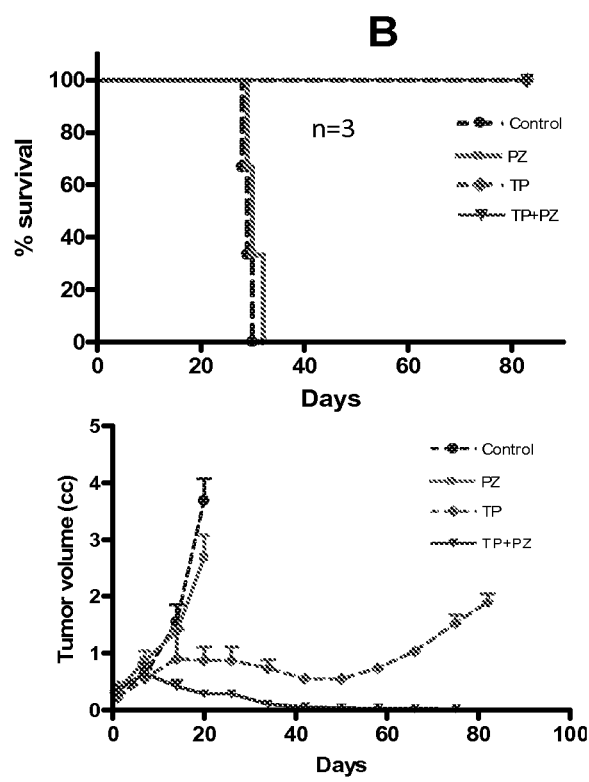
FIG. 9B illustrates a Kaplan Meier survival curve (top) and a tumor growth rate curve (bottom) for the NB12 xenograft model.

Efficacy of TP or TP+PZ in Reducing Tumor Growth Rate in TICs NB12 Xenograft Model In the NB12 xenograft model, palpable tumors started appearing three weeks after implantation. No significant difference was observed between the control group and PZ group (FIG. 9B). However, tumor growth was significantly reduced in the TP and TP+PZ treatment groups, and survival significantly enhanced, compared to control and PZ groups (P<0.005). The animals in TP and TP+PZ groups were treated until day 83, after which they were sacrificed.

Figure 9C:
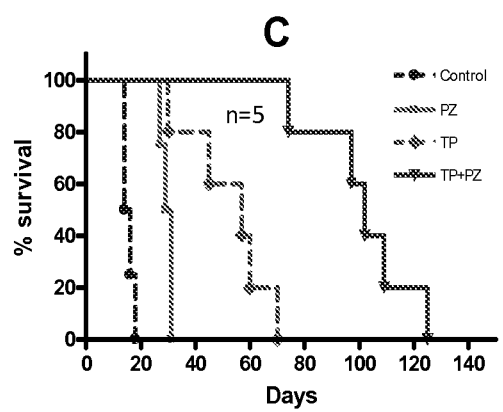
FIG. 9C illustrates a Kaplan Meier survival curve for the BE(2)-c metastatic model.
Figure 10:
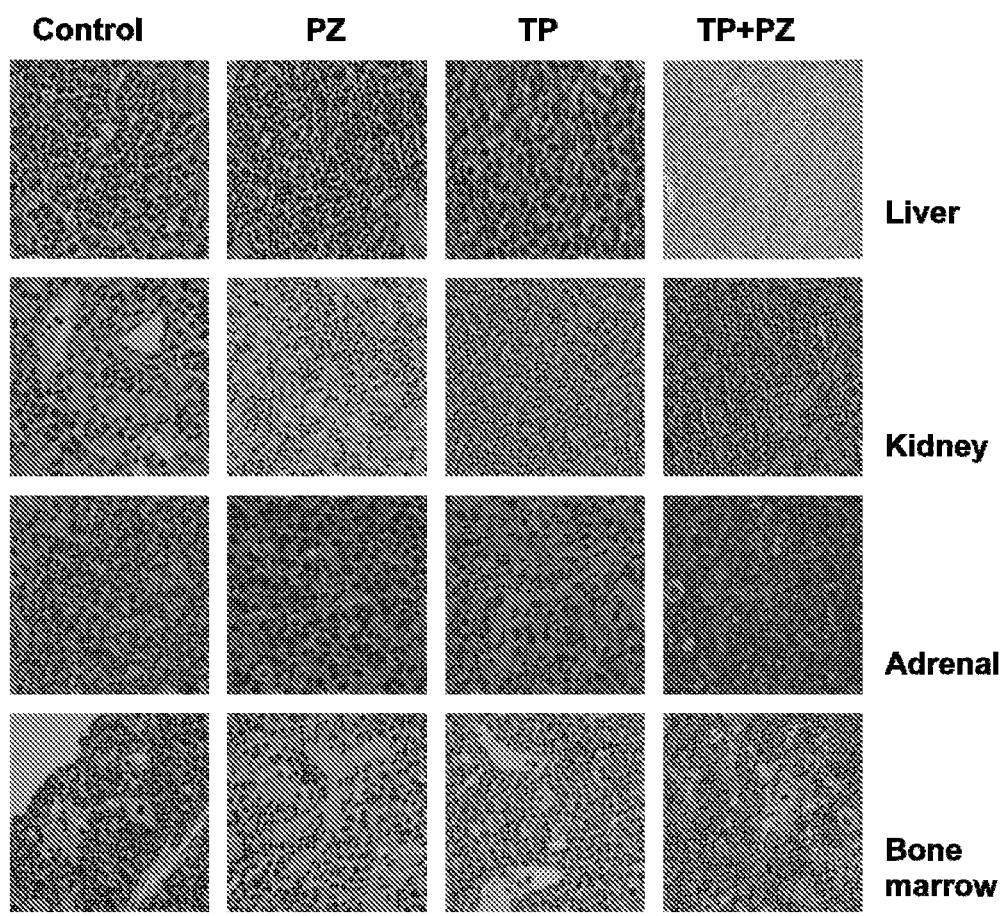
FIG. 10 illustrates histology slides of organs obtained from the animals belonging to the metastatic model.

TP+PZ Causes Two-fold Enhancement in Survival Compare to TP in the BE(2)-c Metastatic Tumor Model BE(2)-c cells are N-Myc amplified, 1-type malignant cells which have high potential to migrate and metastasize. Survival time was used as the parameter to assess the efficacy of treatments in the BE(2)-c metastatic model we used. In the BE(2)-c metastatic model, all three treatment groups had significantly higher life span than the control group (P<0.005). The survival span of the TP treated group was higher than the PZ treated group. (P<0.05). The TP+PZ group had a significantly higher survival span compared to both single agents (P<0.005). The mean survival span of animals in TP+PZ group was approximately two fold (100.8 days) compared to the TP treatment group (52.4 days) (FIG. 9C). Histology of organs (FIG. 10) revealed that at the time of death or end point, animals belonging to control, PZ and TP groups had macroscopically detectable tumors in liver and kidney. However, the livers of animals belonging to TP+PZ did not even have microscopic tumor present. The animals in all the four groups had evidence of tumor present in adrenal gland and bone marrow.

Figure 11:
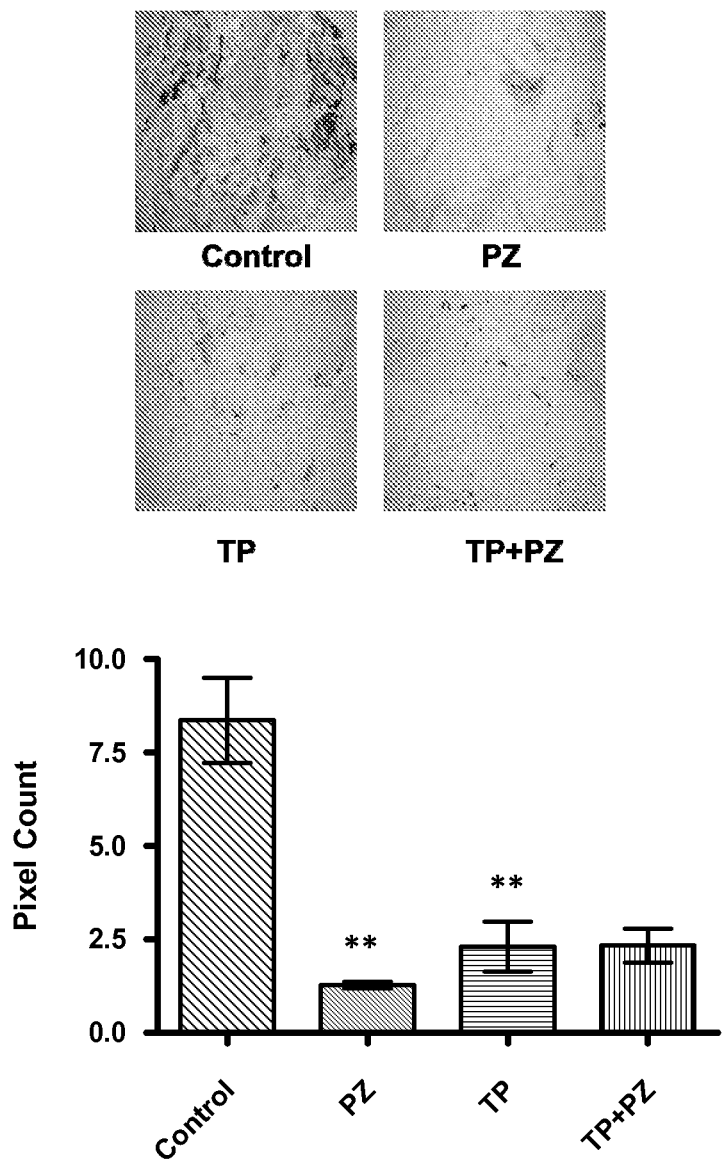
FIG. 11 illustrates von Willebrand Factor stained slides from SK-N-BE(2) xenograft tumor sections, below which lies the comparison of pixel counts for von Willebrand factor positive areas shown as a histogram in which ** represents P<0.005 compared to the control.

All the Three Treatment Regimens Cause Significant Reduction in Microvessel Density in SK-N-BE(2) Xenografts Comparison of the pixel count of six fields of high vascular density (FIG. 11) showed that all of the treatment groups had significantly reduced tumor microvascular density compared to the control group. However, no difference was observed between the microvascular densities between the three treatment groups.

TP+PZ Reduces Levels of HIF-1 Alpha and Oct-4 in NB12 Xenografts

HIF-1 alpha and HIF-2 alpha expression, measured by immunohistochemistry, were unaffected by any of the regimens in SK-N-BE(2) xenograft model (data not shown). However in the NB12 xenograft model, PZ caused an increase in HIF-1 alpha while TP+PZ reduced this change (FIG. 12). TP+PZ also reduced the levels of Oct-4 compared to the control (FIG. 14) while the single agent intervention of either drug had no effect. None of the regimens significantly reduced the expression levels of HIF-2 alpha (FIG. 13).

Effect of the Treatments on CECs/CEPs Levels

CEPs are thought to originate from the bone marrow and also the adipose tissue. VEGF stimulates the recruitment of CEPs into the tumor neovasculature and thus contributes to the endothelial lining. Therefore blockade of the VEGF-signalling pathway is expected to reduce the CEP level in blood and thus inhibit angiogenesis.

Figure 15:
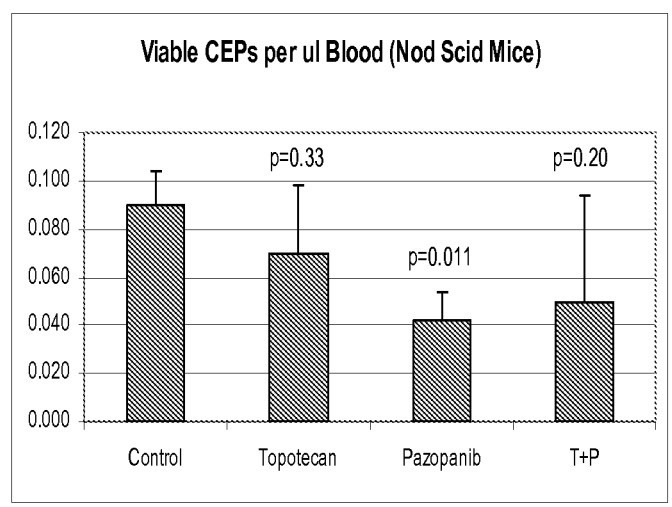
FIG. 15 illustrates a comparison of viable CEP levels in the SK-N-BE(2) xenograft model after 1 week of treatment. The Y-axis shows the levels of CEP per µl of blood.
Figure 16:
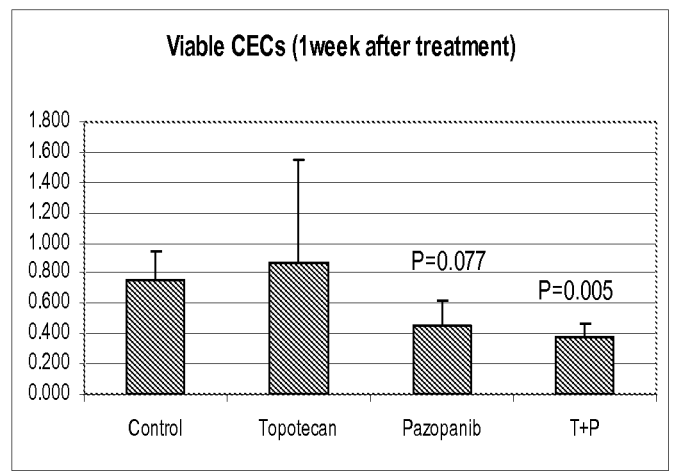
FIG. 16 illustrates a comparison of viable CEC levels in the BE2(c) metastatic model after 1 week of treatment. The Y-axis shows the levels of CEC per µl of blood.
Figure 17:
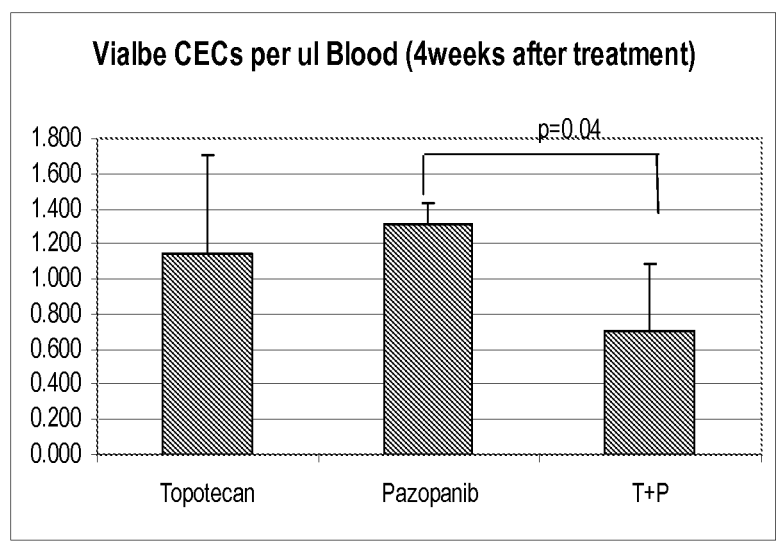
FIG. 17 illustrates a comparison of viable CEC levels in the BE2(c) metastatic model after 4 weeks of treatment. The Y-axis shows the levels of CEC per µl of blood.
Figure 18:
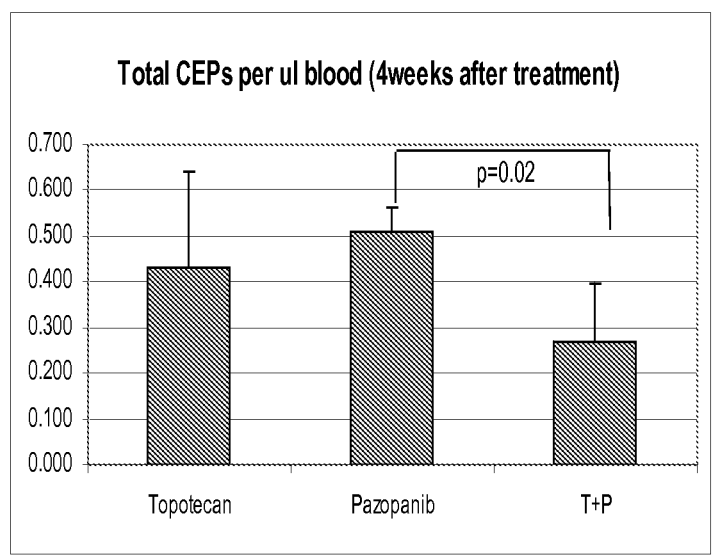
FIG. 18 illustrates a comparison of viable CEP levels in the BE2(c) metastatic model after 4 weeks of treatment. The Y-axis shows the levels of CEC per µl of blood.
Figure 19:
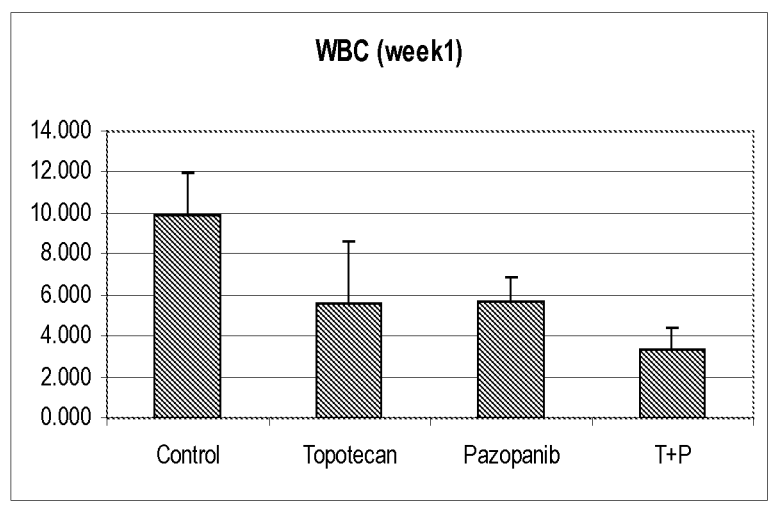
FIG. 19 illustrates the WBC counts after 1 week of treatment in the BE2(c) metastatic model after 4 weeks of treatment.
Figure 20:
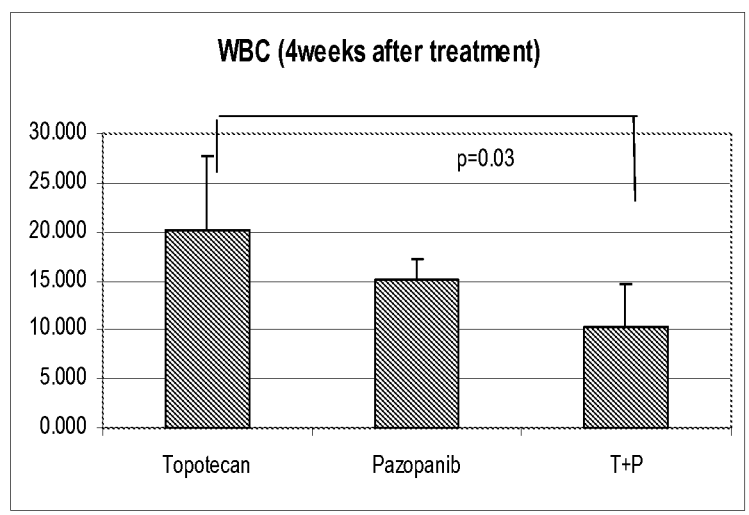
FIG. 20 illustrates the WBC counts after 4 weeks of treatment in the BE2(c) metastatic model after 4 weeks of treatment.

Here, after one week treatment, the mean values of CEPs decreased compared to control in all three treatment groups, with statistically significant difference in the PZ treated group of SK-N-BE(2) xenograft model (FIG. 15). In the BE(2)-c metastatic model, TP+PZ showed as well a significant reduction in viable CEC levels after one week treatment (FIG. 16). None of the animals in control group were alive in metastatic model after four weeks, therefore comparison between treatment groups and control could not be made. In the metastatic model, four weeks treatment with TP+PZ significantly reduced the levels of viable CECs and total CEPs compared to treatment with PZ alone (FIGS. 17 and 18).

Figure 22:
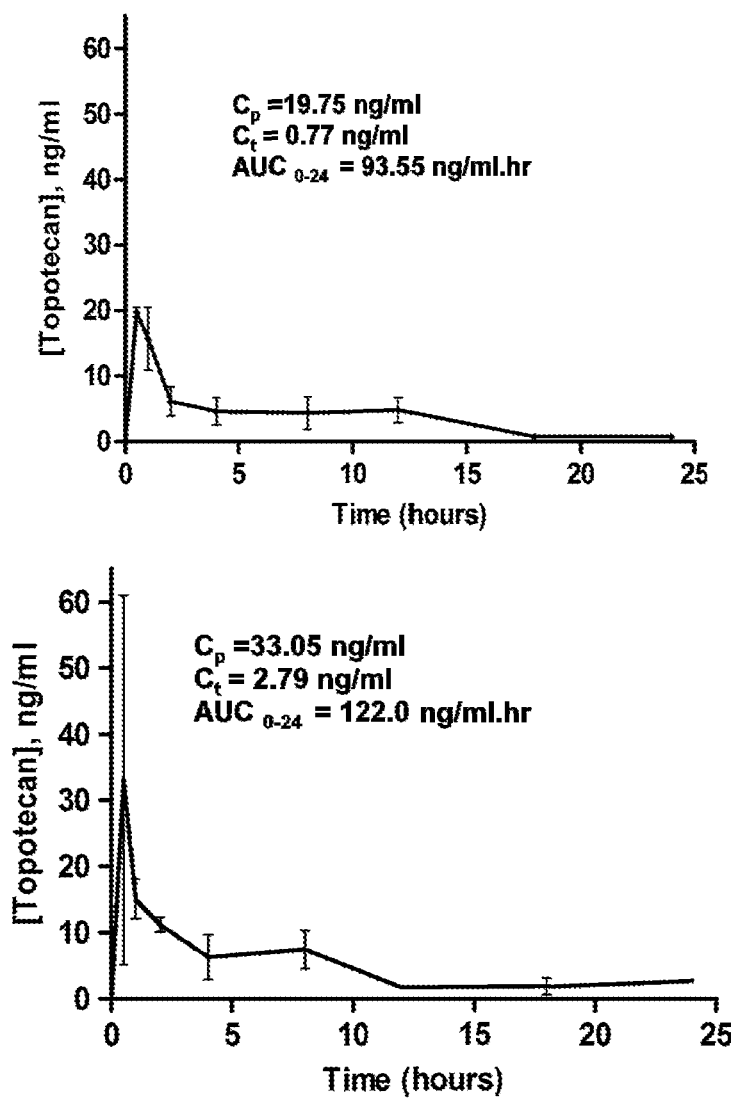
FIG. 22 illustrates the plasma concentration-time profile of topotecan in the single agent group (PZ) (top graph) and the plasma concentration-time profile of topotecan in the combination group (TP+PZ) group (bottom graph), where $C_t$ is peak plasma concentration and $C_t$ is trough plasma concentration.

PK Did not Reveal Drug Interaction between Topotecan and Pazopanib in TP+PZ Group The PK of topotecan and pazopanib was conducted to detect any pharmacokinetic interaction between topotecan and pazopanib in TP+PZ group. The peak plasma concentration of pazopanib was reached in 2 h (FIG. 21) in both PZ and TP+PZ groups. The Cmax was 133.50 ng/ml and 122.43 ng/ml in PZ and TP+PZ groups respectively, while the trough concentration was 9.46 ng/ml and 14.56 ng/ml respectively. Peak plasma concentrations of topotecan in TP and TP+PZ groups was 19.75 ng/ml and 33.05 ng/ml, respectively, while the trough concentration was 0.77 ng/ml and 2.79 ng/ml (FIG. 22). For both drugs, no significant difference was observed between plasma concentrations of single agent and combination treated animals at any time point A significant inter-animal drug concentration variability was detected and larger group studies may be necessary to detect drug-drug interactions and changes in trough concentration. The previously reported optimal plasma concentration of pazopanib effectiveness (40 µM or ≈18 µg/ml) was maintained until at least 18 h in both PZ and TP+PZ groups.

Osteosarcoma and Rhabdomyosarcoma

In-vitro Dose-response of Topotecan on Osteosarcoma Cell Lines (KHOS) and Rhabdomyosarcoma Cell Lines (Rh30, Rh4 and RD)

Materials: The cells were cultured at 37° C. in 5% CO2 in a-MEM (Multicell; Wisent, Inc., St. Bruno, Quebec, Canada) with 10% fetal bovine serum (FBS; Life Technologies, Grand Island, N.Y.) and 1% antibiotic mixture, containing 10000 IU penicillin and 10000 µg/ml streptomycin (Multicell; Wisent, Inc., St. Bruno, Quebec, Canada). Trypsin-EDTA, containing 0.05% trypsin and 0.53 mM EDTA was also purchased from Multicell; Wisent, Inc., St. Bruno, Quebec, Canada. Topotecan hydrochloride and pazopanib hydrochloride were obtained from GlaxoSmithKline.

Procedure: A total of 20,000 cells were plated in each well of 48 well-plates and incubated at 37° C. in 5% CO2. After 48 h, the cells were treated with various concentrations of drugs. After 72 h of treatment, the cell viability was determined by alamar blue assay.

Figure 23B:
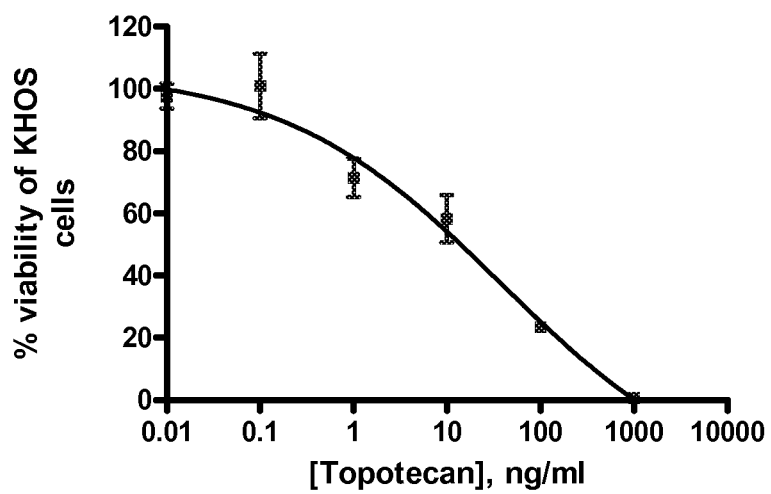
FIG. 23B illustrates the in vitro dose-response curves of topotecan on osteosarcoma cell lines (KHOS) after 72 h treatment.

Results: Topotecan demonstrated dose-dependent reduction in viabilities of KHOS (FIG. 23B), Rh30 and RD cell lines (FIG. 23A), but not Rh4 upto the concentration of 1000 ng/ml. Pazopanib did not show cytotoxicity at any of the concentrations.

In-vivo Efficacy of Pulse Topotecan, LDM Topotecan and the Combination of LDM Topotecan and Pazopanib in Osteosarcoma/Rhabdomyosarcoma Mouse Xenograft Model after Treatment for 27 Days Procedure: 1×10⁶ KHOS cells were implanted into the subcutaneous fat pad of each of NOD/SCID mice. Treatment was started when the tumors reached 0.5 cm in diameter. The animals were randomized into 4 groups, (n=5): Control, Pulse topotecan (15 mg/Kg), LDM topotecan (1.0 mg/kg) and the combination (1.0 mg/Kg topotecan and 150 mg/Kg pazopanib The duration of daily oral treatment was 27 days for osteosarcoma, after which all the animals were sacrificed.

Figure 24A:
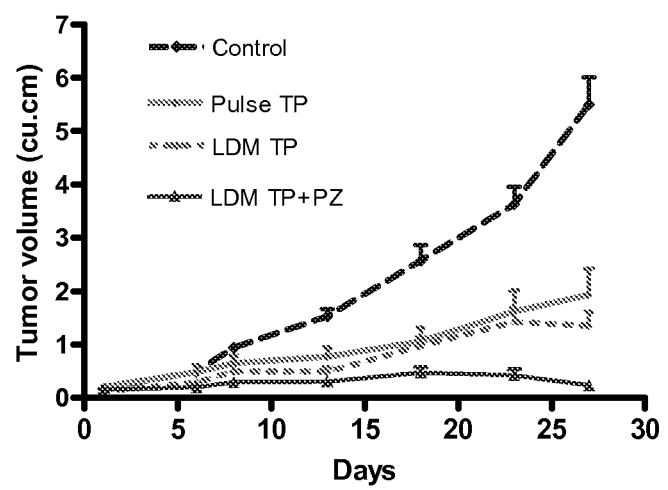
FIG. 24A illustrates the in vivo efficacies of pulse topotecan (Pulse TP), low dose metronomic topotecan (LDM TP) and the combination of LDM TP and pazopanib (LDM TP+PZ) as a comparison of tumor growth rate in mice that were sacrificed after 27 days treatment in KHOS osteosarcoma model.
Figure 24B:
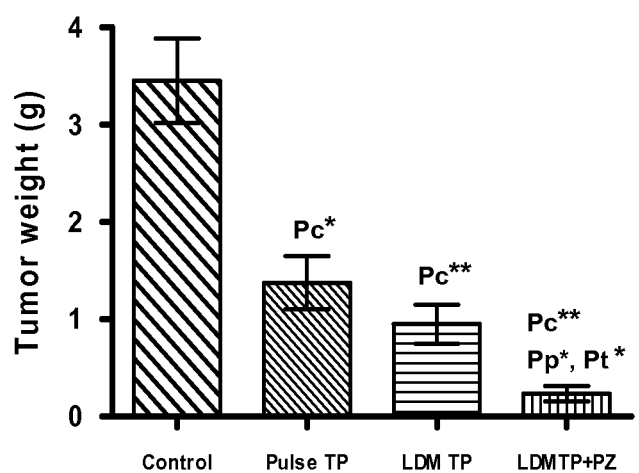
FIG. 24B illustrates the in vivo efficacies of pulse topotecan (Pulse TP), low dose metronomic topotecan (LDM TP) and the combination of LDM TP and pazopanib (LDM TP+PZ) as a comparison of tumor weights in mice that were sacrificed after 27 days treatment in KHOS osteosarcoma model. Pc, Pp and Pt are the P values compared to control, pulse topotecan and LDM topotecan respectively. P<0.05; ** P<0.005.

Results: All the three treatment regimens (Pulse topotecan, LDM topotecan and the combination) delayed the tumor growth rate (FIG. 24A). No significant differences were observed between the tumor weights of Pulse and LDM topotecan. The combination significantly reduced the tumor weights in comparison to both pulse and LDM topotecan (FIG. 24B).

Measurement of Viable Circulating Endothelial Cells (CECs) and Circulating Endothelial Progenitor Cells (CEPs) in KHOS Osteosarcoma Model after 21 Days Treatment Procedure: Approximately 160 µl of blood was sampled in heparinized microtubes at 21st day of treatment by saphenous vein puncturing. These blood samples were stored at 4° C. until analysis. CEC/CEP measurement was done within 48 h of blood collection by flow cytometry.

Figure 25A:
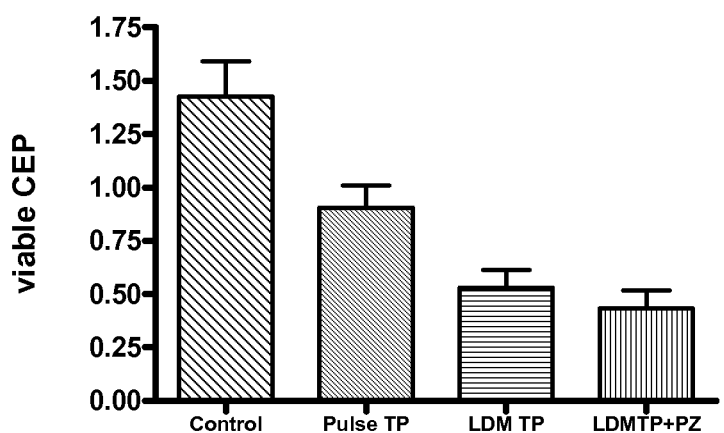
FIG. 25A illustrates measurement of viable CEPs after 21 days treatment in the osteosarcoma KHOS model.
Figure 25B:
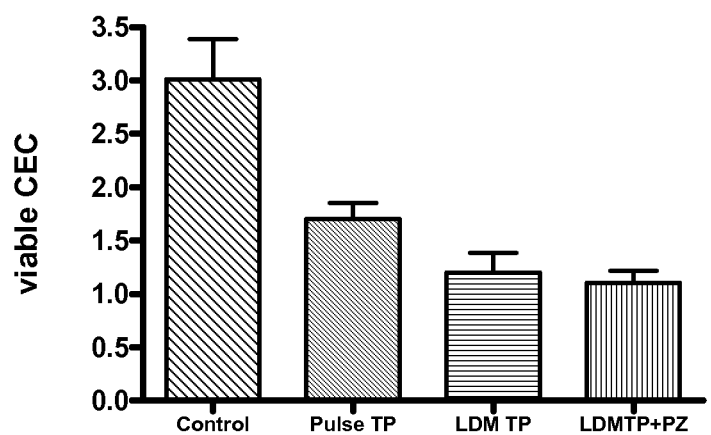
FIG. 25B illustrates measurement of viable CECs after 21 days treatment in the osteosarcoma KHOS model.
Figure 25C:
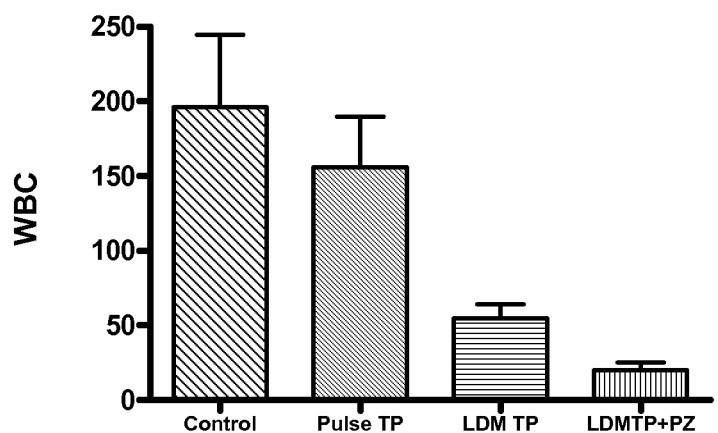
FIG. 25C illustrates measurement of WBCs after 21 days treatment in the osteosarcoma KHOS model.

Result: All the three regimens (Pulse TP, LDM TP and TP+PZ) significantly reduced the levels of viable CECs and CEPs. Viable CEP and White Blood Cell (WBC) levels of LDM TP were significantly lower than pulse TP. TP+PZ caused significant reduction of viable CEPs, CECs and WBC, compared to pulse TP. However, the reduction of CECs and CEPs by TP+PZ was not significant compared to LDM TP Results are shown in FIGS. 25A-C and in Table 1.

TABLE 1

|  | CEC | CEP | WBC |
|---|---|---|---|
| Control vs Pulse | * | * | NS |
| Control vs TP | ** | ** | * |
| Control vs TP + PZ | ** | *** | ** |
| Pulse vs TP | NS | * | * |
| Pulse vs TP + PZ | * | * | ** |
| TP vs TP + PZ | NS | NS | * |

NS = not significant
* P < 0.05
** P < 0.005
*** P < 0.001

Measurement of Microvessel Density by Von Willebrand Factor Staining of KHOS Osteosarcoma Tumor Xenografts after 28 Days Treatment Procedure: Formalin fixed tissues were paraffin embedded and sections cut at 7 um. These paraffin embedded sections were deparaffinized through xylene and ethanol, rehydrated in Phosphate-buffered Saline (PBS) (#311-0,0-CL, Wisent Bioproducts) and incubated overnight with primary antibodies at 4° C. The primary antibody was von Willebrand factor (#A0082; DakoCytomation, Glostrup, Denmark). After the primary antibody treatment, the slides were washed three times with PBS and incubated with broad spectrum polyhorse radish peroxidase (HRP) conjugate secondary antibody (87-9663, Invitrogen) for 1 h at room temperature. After washing three times with PBS, slides were stained with diaminobenzidine (DAB) and counterstained with hematoxylin. Microscopic images of six fields of high vascular density were digitally captured. The pixel values for stained areas were quantified using ImageJ software. Tumor angiogenesis was quantified as the number of pixels of regions positive for von Willebrand Factor.

Figure 26:
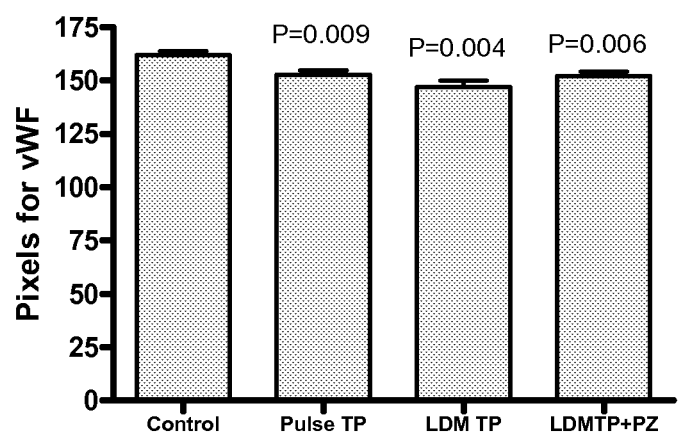
FIG. 26 illustrates microvessel density measurement of KHOS osteosarcoma xenografts by von Willebrand Factor staining.

Result: The microvessel densities of all three groups in osteosarcoma model (Pulse TP, LDM TP and TP+PZ) were significantly lower than the control. No significant difference was observed between the microvessel densities of three treatment groups (FIG. 26).

In-vivo Efficacy of Pazopanib, LDM Topotecan and the Combination of LDM Topotecan And Pazopanib in RH30 Rhabdomyosarcoma Mouse Xenograft Model Procedure: 1×10⁶ Rh30 cells were implanted into the subcutaneous fat pad of each of NOD/SCID mice. Treatment was started when the tumors reached 0.5 cm in diameter. The animals were randomized as (n=5): Control, Pazopanib or PZ (150 mg/Kg), LDM topotecan or TP (1.0 mg/kg) and the combination or TP+PZ (1.0 mg/Kg topotecan and 150 mg/Kg pazopanib). The duration of daily oral treatment was 56 days oe till the end point (whichever was earlier). The mice which survived after 56 days treatment are kept under observation. A fifth group (n=4) was added to this study, which was treated with intermittent dosing (every 3 days) of pazopanib (150 mg/Kg) and topotecan (7.5 mg/Kg). In this group topotecan was administered on the subsequent day of pazopanib dosing. The hypothesis for intermittent dosing of drugs is that intermittent pazopanib dosing will sustain the vascular normalization without disrupting the vasculature. Topotecan administered at half the maximal dosing of topotecan on the subsequent day will be able to penetrate better into the tumor. As a result, the cytotoxicity to tumor cells will be enhanced compared to daily combined dosing.

Figure 27:
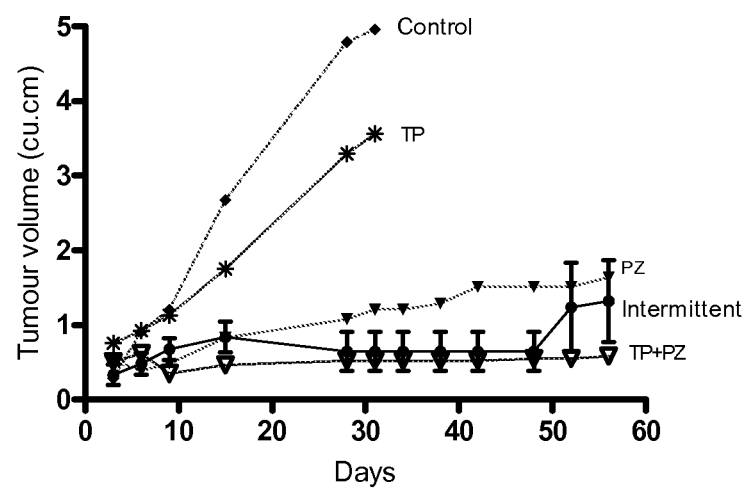
FIG. 27 illustrates tumor growth rate in RH30 rhabdomyosarcoma model.
Figure 28:
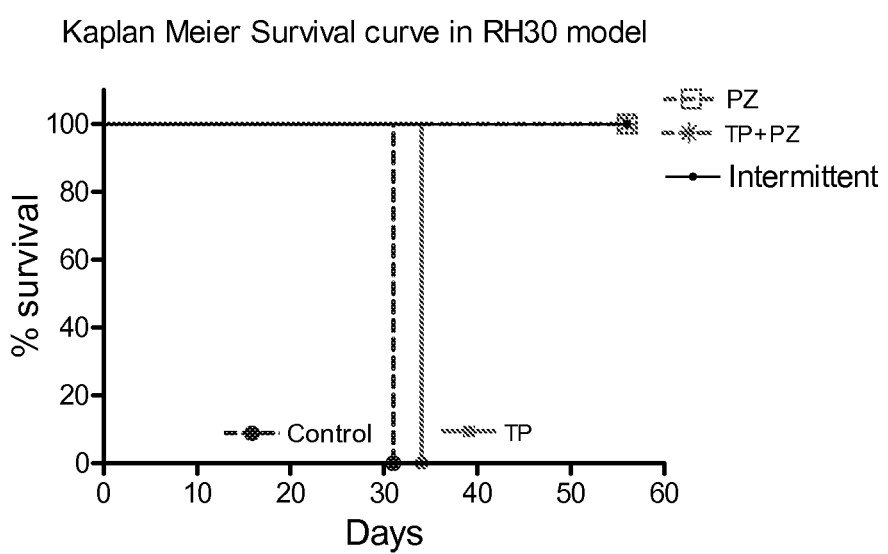
FIG. 28 illustrates a Kaplan Meier Survival curve in RH30 rhabdomyosarcoma model.

Results: All the four treatment regimens (pazopanib, LDM topotecan and the combination) delayed the tumor growth rate. However unlike osteosarcoma model, LDM topotecan was less effective than PZ, TP+PZ and intermittent dosing of topotecan and pazopanib. So far no significant difference has been observed between PZ and intermittent dosing, while TP+PZ has significantly higher efficacy than both in terms of tumor growth reduction (P<0.05) (FIG. 27) and in survival (FIG. 28).

While the preferred embodiments of the invention are illustrated by the above, it is to be understood that the invention is not limited to the precise instructions herein disclosed and that the right to all modifications coming within the scope of the following claims is reserved.

We claim:

1. A combination comprising:
(i) a compound of Structure (I):

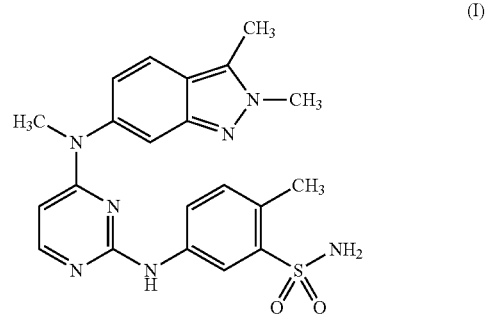 [SMILES: Cc1ccc(Nc2nccc(N(C)c3ccc4c(C)n(C)nc4c3)n2)cc1S(N)(=O)=O]

or a pharmaceutically acceptable salt thereof; and (ii) a compound of Structure (II):

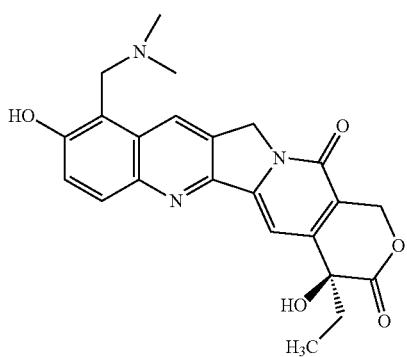

(II)

or a pharmaceutically acceptable salt thereof.

2. A combination according to claim 1 where the compounds of Structure (I) and Structure (II) are each in the form of a monohydrochloride salt.

3. A method treating neuroblastoma in a human in need thereof, comprising the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt thereof, and (S)-10-[(dimethylamino)methyl]-4-ethyl-4,9-dihydroxy-1H-pyrano[3',4':6,7] indolizino [1,2-b]quinoline-3,14-(4H,12H)-dione, or a pharmaceutically acceptable salt thereof, to such human, wherein the compounds of the combination are administered sequentially.

4. A method according to claim 3, wherein 5-[[4-[(2,3-dimethyl-2H-indazol-6-yl)methylamino]-2-pyrimidinyl]amino]-2-methylbenzenesulfonamide and (S)-10-[(dimethylamino)methyl]-4-ethyl-4,9-dihydroxy-1H-pyrano[3',4':6,7] indolizino [1,2-b]quinoline-3,14-(4H,12H)-dione are each in the form of a monohydrochloride salt.

5. A pharmaceutical composition comprising a combination of 5[[4-[(2,3-dimethyl-2H-indazol-6-yl)methylamino]-2-pyrimidinyl]amino]-2-methylbenzenesulfonamide, or a pharmaceutically acceptable salt thereof, and (S)-10-[(dimethylamino)methyl]-4-ethyl-4,9-dihydroxy-1H-pyrano[3',4':6,7] indolizino [1,2-b]quinoline-3,14-(4H,12H)-dione, or a pharmaceutically acceptable salt thereof.

6. A pharmaceutical composition according to claim 5 wherein 5[[4-[(2,3-dimethyl-2H-indazol-6-yl)methylamino]-2-pyrimidinyl]amino]-2-methylbenzenesulfonamide and (S)-10-[(dimethylamino)methyl]-4-ethyl-4,9-dihydroxy-1H-pyrano[3',4':6,7] indolizino [1,2-b]quinoline-3,14-(4H,12H)-dione are each in the form of a monohydrochloride salt.

7. A method treating osteosarcoma in a human in need thereof, comprising the in vivo administration of a therapeutically effective amount of a combination of 5-[[4-[(2,3-dimethyl-2H-indazol-6-yl)methylamino]-2-pyrimidinyl]amino]-2-methylbenzenesulfonamide, or a pharmaceutically acceptable salt thereof, and (S)-10-[(dimethylamino)methyl]-4-ethyl-4,9-dihydroxy-1H-pyrano[3', 4':6,7] indolizino [1,2-b]quinoline-3,14-(4H,12H)-dione, or a pharmaceutically acceptable salt thereof, to such human, wherein the compounds of the combination are administered sequentially.

8. A method according to claim 7, wherein 5-[[4-[(2,3-dimethyl-2H-indazol-6-yl)methylamino]-2-pyrimidinyl]amino]-2-methylbenzenesulfonamide and (S)-10-[(dimethylamino)methyl]-4-ethyl-4,9-dihydroxy-1H-pyrano[3',4':6,7] indolizino [1,2-b]guinoline-3,14-(4H,12H)-dione are each in the form of a monohydrochloride salt.

9. A method of treating rhabdomyosarcoma in a human in need thereof, comprising the in vivo administration of a therapeutically effective amount of a combination of 5[[4-[(2,3-dimethyl-2H-indazol-6-yl)methylamino]-2-pyrimidinyl]amino]-2-methylbenzenesulfonamide, or a pharmaceutically acceptable salt thereof, and (S)-10-[(dimethylamino)methyl]-4-ethyl-4,9-dihydroxy-1H-pyrano[3',4':6,7] indolizino [1,2-b]quinoline-3,14-(4H,12H)-dione, or a pharmaceutically acceptable salt thereof, to such human, wherein the compounds of the combination are administered sequentially.

10. A method according to claim 9, wherein 5-[[4-[(2,3-dimethyl-2H-indazol-6-yl)methylamino]-2-pyrimidinyl]amino]-2-methylbenzenesulfonamide and (S)-10-[(dimethylamino)methyl]-4-ethyl-4,9-dihydroxy-1H-pyrano[3',4':6,7] indolizino [1,2-b]guinoline-3,14-(4H,12H)-dione are each in the form of a monohydrochloride salt.

* * * * *